US009173994B2

(12) United States Patent
Ziaie et al.

(10) Patent No.: US 9,173,994 B2
(45) Date of Patent: Nov. 3, 2015

(54) TOUCH-ACTUATED MICROPUMP FOR TRANSDERMAL DRUG DELIVERY AND METHOD OF USE

(75) Inventors: Babak Ziaie, West Lafayette, IN (US); Manuel Ochoa, West Lafayette, IN (US); Charilaos Mousoulis, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 1025 days.

(21) Appl. No.: 13/214,990

(22) Filed: Aug. 22, 2011

(65) Prior Publication Data
US 2012/0046644 A1 Feb. 23, 2012

Related U.S. Application Data

(60) Provisional application No. 61/375,575, filed on Aug. 20, 2010, provisional application No. 61/406,875, filed on Oct. 26, 2010.

(51) Int. Cl.
*A61M 5/142* (2006.01)
*A61M 5/145* (2006.01)
*A61M 37/00* (2006.01)

(52) U.S. Cl.
CPC ....... *A61M 5/14248* (2013.01); *A61M 5/14586* (2013.01); *A61M 5/14593* (2013.01); *A61M 2037/003* (2013.01); *A61M 2037/0023* (2013.01)

(58) Field of Classification Search
CPC .............. A61M 5/14248; A61M 5/14586; A61M 5/14593; A61M 37/0015; A61M 2005/14204; A61M 2037/0023; A61M 2037/003; A61M 2037/0038; A61M 2037/0061; A61M 2205/36; A61M 2205/3613–2205/3693; F04B 43/043

USPC .................................. 604/141, 145, 153, 173
See application file for complete search history.

(56) References Cited

U.S. PATENT DOCUMENTS 4,221,219 A * 9/1980 Tucker .......................... 604/141
5,700,245 A * 12/1997 Sancoff et al. ................ 604/145

(Continued)

FOREIGN PATENT DOCUMENTS

WO   WO2010052692   *   5/2010

OTHER PUBLICATIONS

Anubhav Arora, Mark Prausnitz, and Samir Mitragotri, Micro-scale Devices for Transdermal Drug Delivery, NIH Public Access, Published in final edited form as: Int J Pharm. Dec. 8, 2008, 364(2), 227-236. doi: 10.1016/j.ijpharm.2008.08.032.
A. Nisar, Nitin Afzulpurkar, Banchong Mahaisavariya, Adisorn Tuantranont, MEMS-based micropumps in drug delivery and biomedical applications, ScienceDirect, Sensors and Actuators B 130 (2008) 917-942.

(Continued)

*Primary Examiner* — Kami A Bosworth
(74) *Attorney, Agent, or Firm* — Purdue Research Foundation

(57) ABSTRACT

A micropump device. The micropump device includes a first layer forming a first chamber configured to store a working material, a second chamber defined by a deflectable membrane in fluid communication with the first chamber and configured to deflect in response to a pressure increase in the first chamber in response to a volume increase in the first chamber, the second chamber configured to store a drug compound to be delivered to a subject's vascular system, and at least one needle in fluid communication with the second chamber and configured to penetrate a subject's skin to pump the drug compound in response to the deflection of the deflectable membrane.

8 Claims, 23 Drawing Sheets

(56) References Cited

U.S. PATENT DOCUMENTS

| | | | |
|---|---|---|---|
| 6,200,293 B1 * | 3/2001 | Kriesel et al. | 604/132 |
| 6,283,949 B1 * | 9/2001 | Roorda | 604/288.02 |
| 6,562,004 B1 * | 5/2003 | Doukas et al. | 604/145 |
| 7,108,686 B2 * | 9/2006 | Burke et al. | 604/891.1 |
| 7,429,258 B2 * | 9/2008 | Angel et al. | 604/173 |
| 8,021,357 B2 * | 9/2011 | Tanaka et al. | 604/890.1 |
| 2010/0151099 A1 * | 6/2010 | Kazemzadeh | 426/448 |

OTHER PUBLICATIONS

Wijaya Martanto, Shawn P. Davis, Nicholas R. Holiday, Jenny Wang, Harvinder S. Gill, and Mark R. Prausnitz, Transdermal Delivery of Insulin Using Microneedles in Vivo, Pharmaceutical Research, vol. 21, No. 6, Jun. 2004.

Jessamine Ng Lee, Cheolmin Park, and George M. Whitesides, Solvent Compatability of Poly (dimethylsiloxane)-Based Microfluidic Devices, Anal. Chem. 2003, 75, 6544-6554.

* cited by examiner

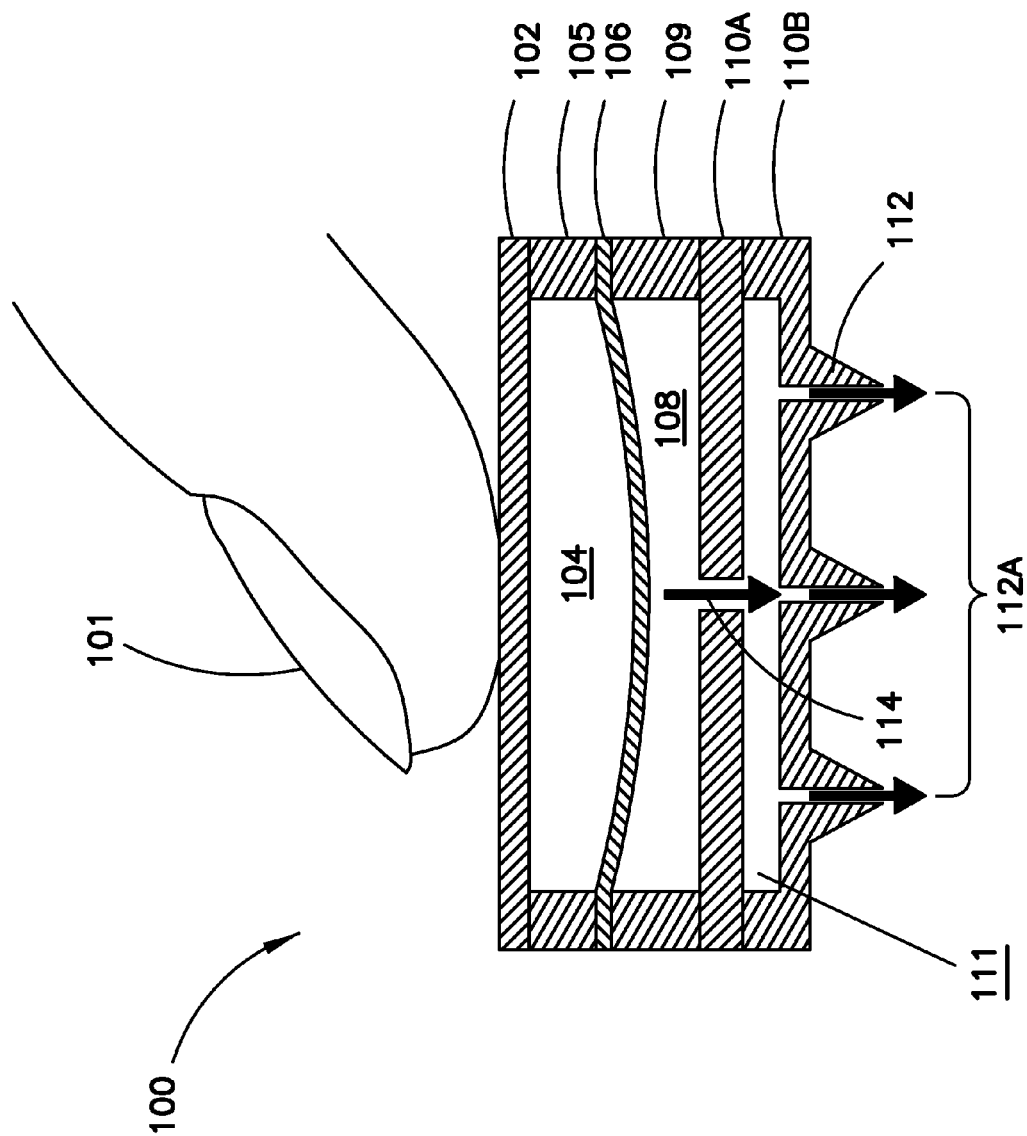

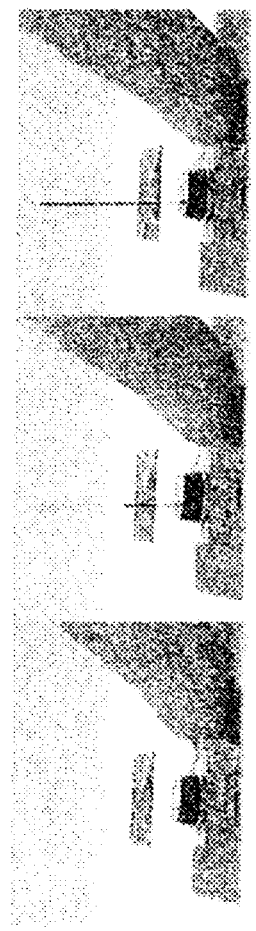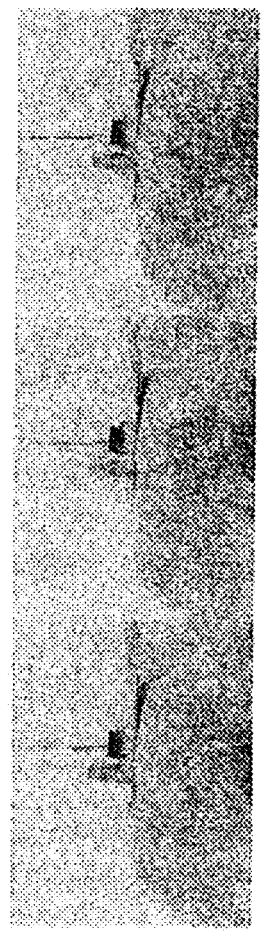

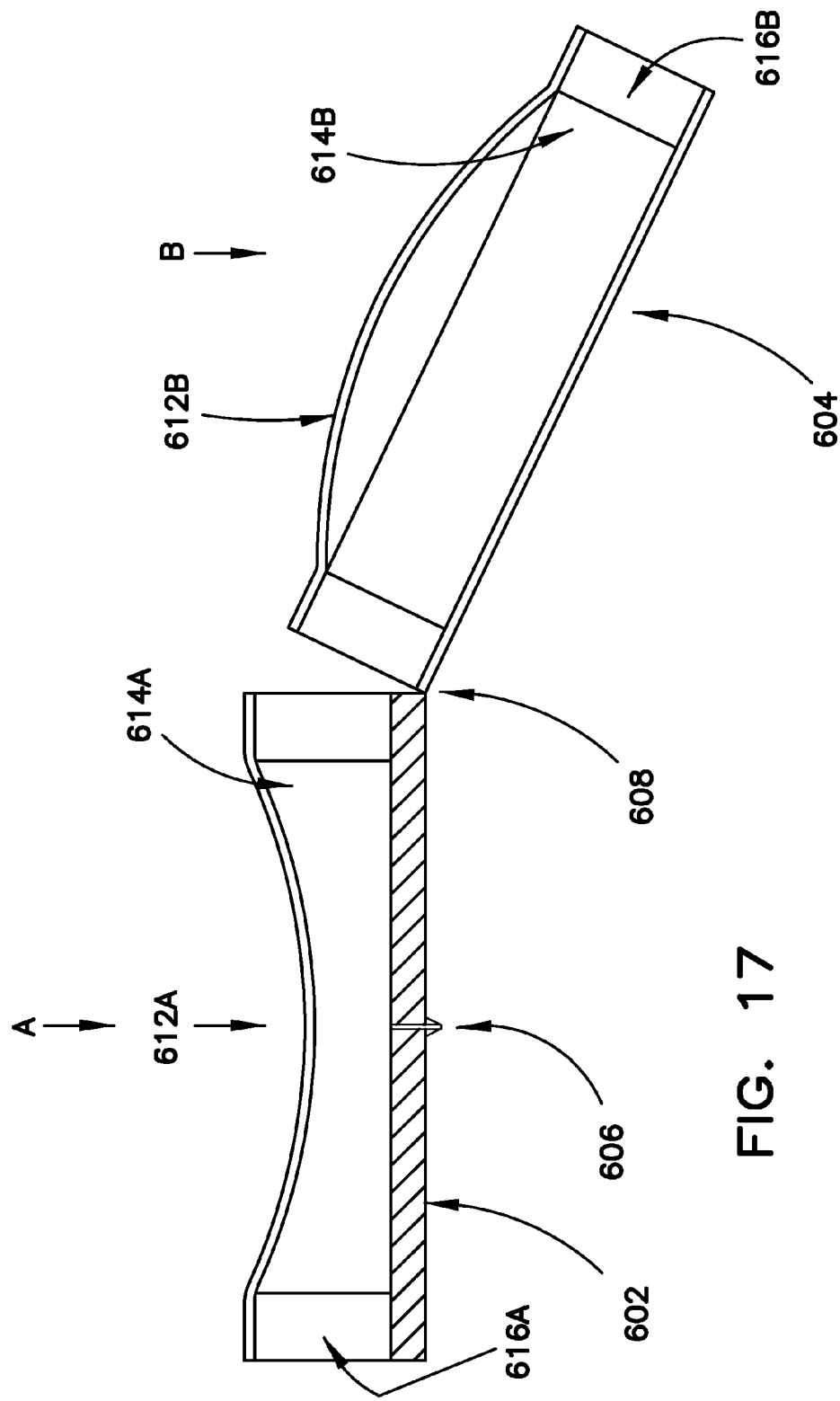

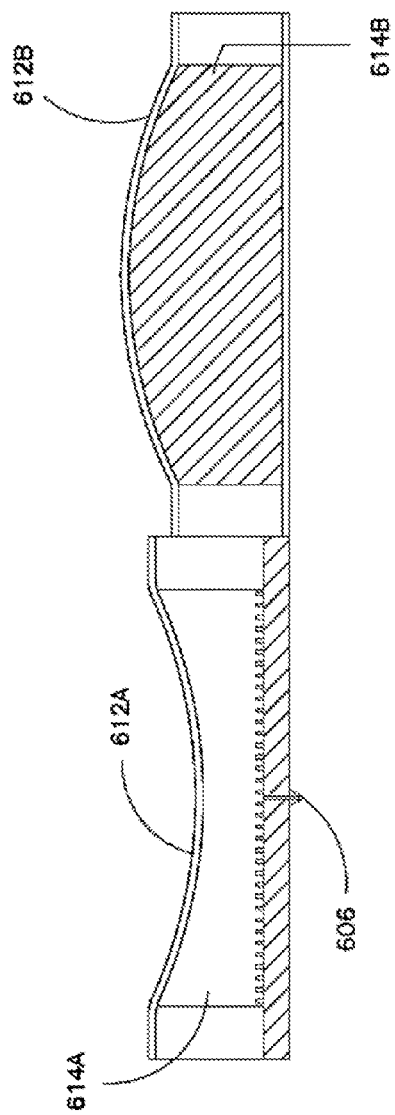
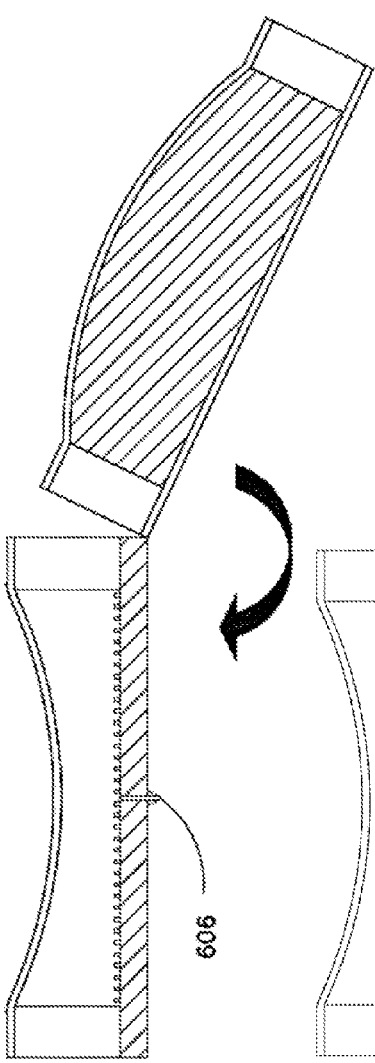
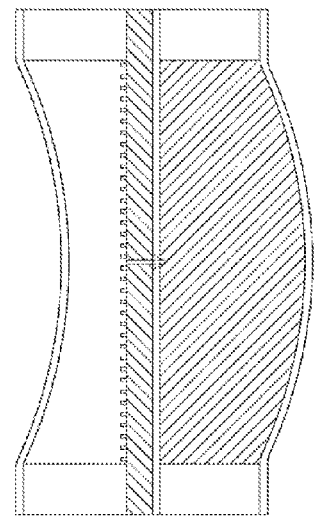
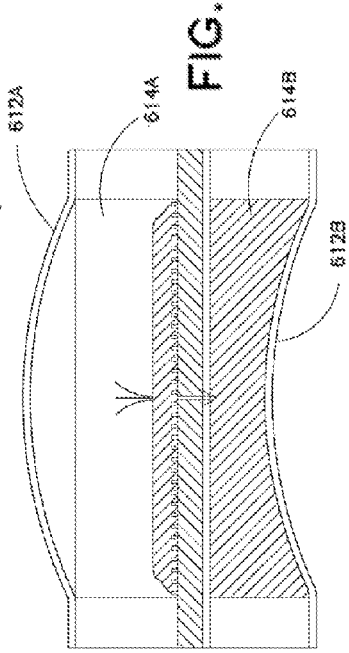
FIG. 18A
FIG. 18B
FIG. 18C
FIG. 18D

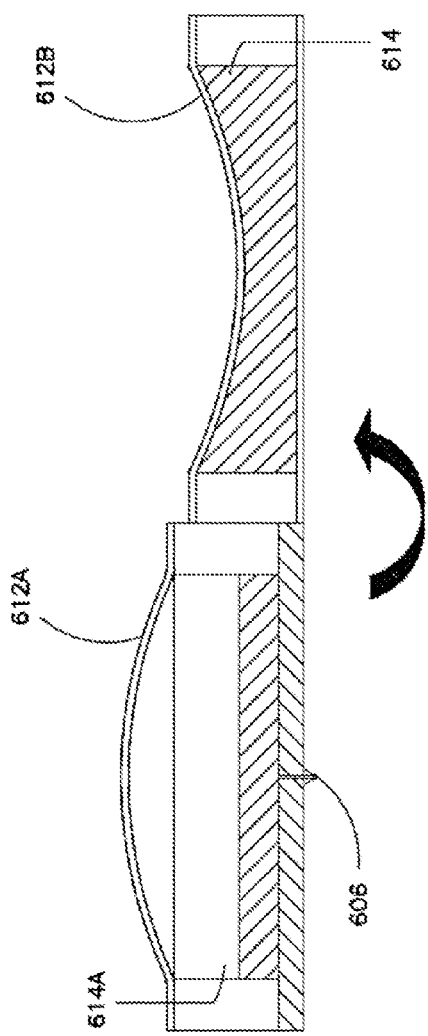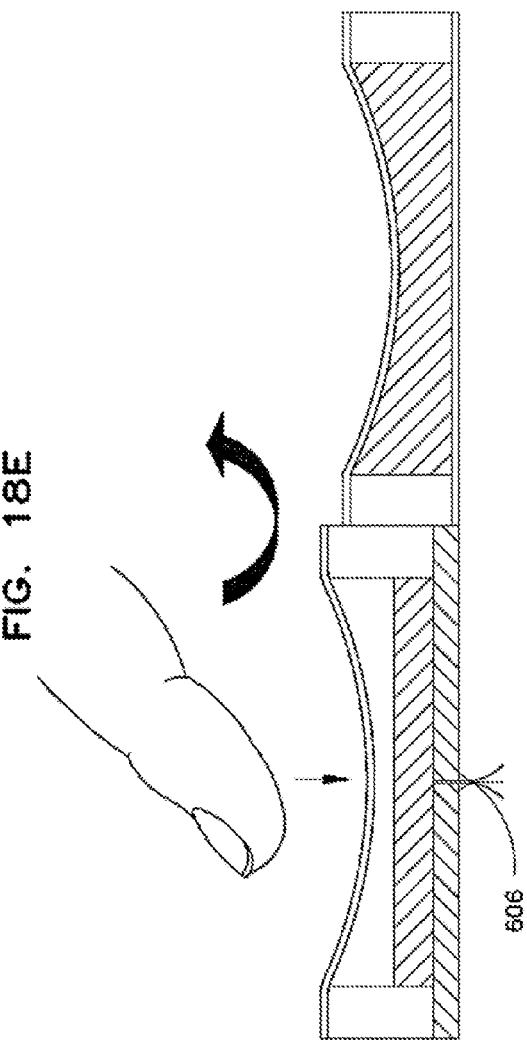

TOUCH-ACTUATED MICROPUMP FOR TRANSDERMAL DRUG DELIVERY AND METHOD OF USE

CROSS REFERENCE TO RELATED APPLICATIONS

The present application is related to, and claims the priority benefit of, U.S. Provisional Patent Application Ser. Nos. 61/375,575 filed Aug. 20, 2010 and 61/406,875 filed Oct. 26, 2010, the contents of which are hereby incorporated in their entirety into the present disclosure.

FEDERALLY SPONSORED RESEARCH

This invention was made with government support under 0753801 awarded by National the Science Foundation. The government has certain rights in the invention.

BACKGROUND

Transdermal delivery of medications and other compounds has been aggressively pursued for many decades. In most of the cases of prior art, an external pressure source in conjunction with a direct subcutaneous access port is typically provided to deliver the medication through the skin. With advancements in the area of microfluidics, micro-scale devices and micropumps for transdermal drug delivery have been developed in the prior art. However, most of the devices rely on electrical to mechanical power transduction in order to dispense the drug, and use of these devices increases the size and complexity of the drug delivery system. Further, the limited shelf life of some drug compounds makes it desirable to have a device that can prepare the compound to be delivered just a short time prior to use. Therefore, a simple, small, and self-powered device is needed for use as a transdermal drug compound delivery system which transfers a drug compound into the capillaries of the vascular system to enter into the blood stream of a subject over both short and extended periods of time or provides multiple doses of a drug compound over time. It is also desirable to be able to prepare the medicinal compound to be administered in its final form within the transdermal pump prior to delivery.

SUMMARY

Various embodiments of a touch-actuated micropump for transdermal drug delivery have been developed. Generally, the transdermal drug compound delivery micropump device according to the present disclosure is configured to deliver at least a dose of a drug compound from a compound chamber to the capillaries of a subject's vascular system to enter into the blood stream of the subject when the device comes in contact with the skin.

According to one aspect of the present disclosure, a micropump device has been disclosed. The micropump includes a first layer forming a first chamber configured to store a working material. The micropump includes a second chamber defined by a deflectable membrane in fluid communication with the first chamber and configured to deflect in response to a pressure increase in the first chamber in response to a volume increase in the first chamber. The second chamber is configured to store a drug compound to be delivered to a subject's vascular system. The micropump also includes at least one needle in fluid communication with the second chamber and configured to penetrate a subject's skin to pump the drug compound in response to the deflection of the deflectable membrane.

According to another aspect of the present disclosure, a micropump device is disclosed. The micropump include a first layer forming at least two chambers separated by a channel and configured to store in the first chamber an activating agent and in the second chamber a reacting material that when mixed together increases volume of the second chamber. The micropump also includes a blocking member disposed in the channel between the first and second chambers configured to i) remain in the channel and thereby separate the activating agent in the first chamber from the reacting agent in the second chamber when the pressure in the first chamber is below a predetermined threshold, and ii) move into the second chamber thereby allowing mixing in the second chamber of the reacting agent in the second chamber with the activating agent arriving from the first chamber when the pressure in the first chamber is equal to or above the predetermined threshold. In addition, the micropump includes a second layer forming a deformable member in fluid communication with the first chamber and configured to deflect in response to application of force to the deformable member, thereby increasing pressure in the first chamber above the predetermined threshold. Furthermore, the micropump includes a third layer comprising a deflectable membrane in fluid communication with the second chamber and configured to deflect in response to a pressure increase in the second chamber. In addition the micropump includes a fourth layer defining a drug compound chamber coupled to the second chamber and configured to store a drug compound and further configured to pump the drug compound into the vascular system and thereby the blood stream of a subject in response to deflection of the deflectable membrane.

According to yet another aspect of the present disclosure, a method for pumping a drug compound into the vascular system of a subject by a micropump is disclosed. The method includes applying heat to a working material positioned in a first chamber and configured to increase volume and thereby pressure in response to the application of heat. The method also include transferring the increase in pressure from the working material to a drug compound positioned in a drug compound chamber. Furthermore, the method includes pumping the drug compound through at least one needle to a vascular system of a subject in response to the transferred pressure.

BRIEF DESCRIPTION OF THE DRAWINGS

FIG. 1A is a fragmentary cross sectional view of a transdermal drug compound delivery micropump device with various layers according to one embodiment of the present disclosure;

FIGS. 3A, 3B, and 3C are perspective views of the transdermal drug compound delivery micropump device of FIG. 1A showing rate of transfer through a capillary tube when a substrate of the device is touched by a finger;

FIGS. 3D, 3E, and 3F are perspective views of the transdermal drug compound delivery micropump device of FIG. 1A showing rate of transfer through a capillary tube when the substrate of the device is in contact with the back of a hand;

FIGS. 16 and 17 depict an exploded view and a side view of another embodiment of a transdermal micropump according to the present disclosure:

FIGS. 18A, 18B, 18C, 18D, 18E, and 18F depict various operational positions of the transdermal micropump of FIGS. 16 and 17;

DETAILED DESCRIPTION

Figure 1B:
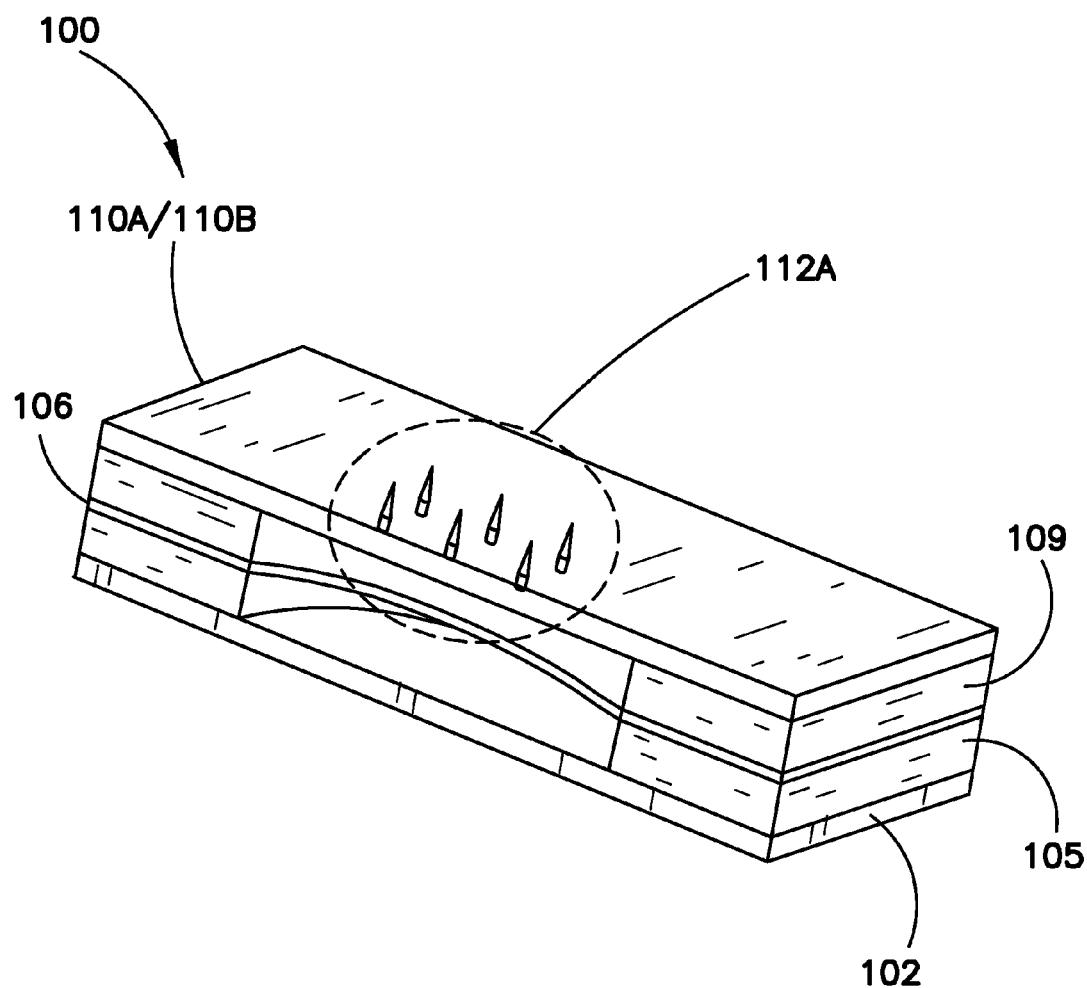
FIG. 1B is a fragmentary perspective view of the transdermal drug compound delivery micropump device of FIG. 1A.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to one of ordinary skill in the art to which this disclosure pertains.

Various embodiments of a touch-actuated micropump for transdermal drug delivery have been developed. Generally, the transdermal drug compound delivery micropump device according to the present disclosure is configured to deliver at least a dose of a drug compound from a compound chamber to the capillaries of a subject's vascular system to enter into the blood stream of the subject when the device comes in contact with the skin.

It should be appreciated that terms "phase-change fluid", "phase-change material" and "working material" are intended to identify the same material, and further this same material can be in the form of solid, liquid, or gas in a starting form. Therefore, the phase-change material can be initially a solid and turn into a liquid, or initially be a liquid and turn into a gas, or simply remain in the same phase, however, change volume by application of heat.

Figure 2:
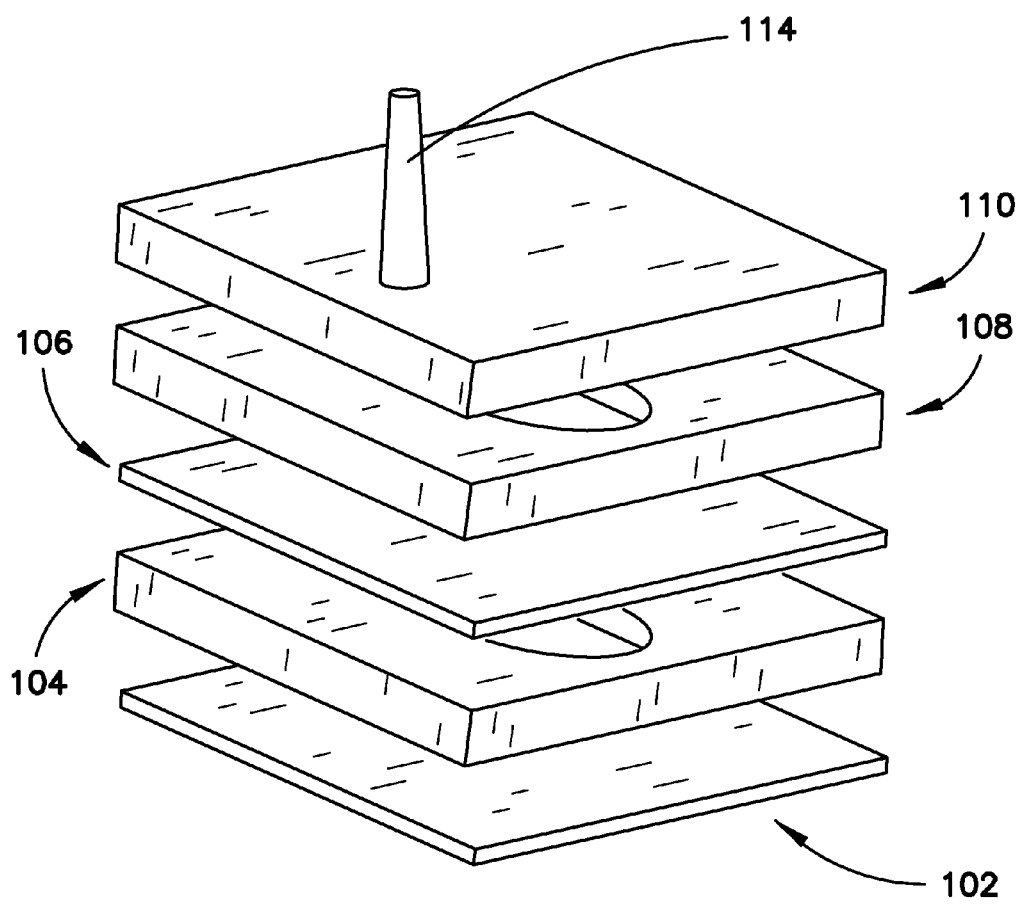
FIG. 2 is a perspective exploded view of the layers forming the transdermal drug compound delivery micropump device of FIG. 1A.

Referring to FIGS. 1A, 1B, and 2, cross sectional, fragmentary, and exploded perspective views of a transdermal drug compound delivery micropump device (the "micropump") 100 according to the present disclosure are depicted. The micropump 100 includes and is defined by a phase-change fluid chamber 104 and a compound chamber 108 separated by a deflectable membrane 106, and by a compound delivery chamber 111.

The phase-change fluid chamber 104 is defined by a cylindrical phase-change fluid chamber wall 105, a thermally conductive substrate 102 on one side, and the deflectable membrane 106 on the opposing side.

The thermally conductive substrate 102 may be made of a highly, thermally conductive material, such as silicon. Metallic substrates (e.g., copper, gold, and other substrate materials often found in microfabrication processes) may also be used as long as the thermally conductive substrate 102 is biocompatible and compatible with the other materials in the device, including the drug compound to be administered.

The phase-change fluid chamber 104 is configured to store a material that readily and substantially changes volume in response to heat. Such a material may be a phase-change fluid, which changes phase (e.g., evaporates) within the temperature range between slightly below room temperature and the surface temperature of a subject's skin.

The deflectable membrane 106 is in contact with the phase-change fluid chamber 104 and the compound chamber 108 and is configured to deflect when the material inside the phase-change fluid chamber 104 changes phase, thereby exerting pressure on the deflectable membrane 106 to deflect it and thereby exerting pressure on the fluid in the compound chamber 108.

The compound chamber 108 is defined by the deflectable membrane 106 on one side and a surrounding sealing cap 110 on the opposite side. The compound chamber 108 is further defined by a chamber wall 109 that is in contact with and seals against the deflectable membrane 106 and the sealing cap 110. The compound chamber 108 is configured to store a volume of a drug compound that is to be delivered via the micropump 100.

The sealing cap 110 includes a top portion 110A and a bottom portion 110B the space between the top portion 110A and the bottom portion 110B defined the compound delivery chamber 111. The top portion 110A includes at least one through hole 114 that provides a flow channel between the compound chamber 108 and the compound delivery chamber 111, and further to at least one needle 112.

In operation, the application of heat via contact between the thermally conductive substrate 102 and the skin surface 101 of a subject causes the phase-change fluid in the phase-change fluid chamber 104 to change phase, such as from a liquid to gas through evaporation. The change in phase increases the volume of the phase-change fluid in the phase-change fluid chamber 104, which causes deflection of the deflectable membrane 106. The deflection of the membrane 106 exerts pressure on the fluid present in the compound chamber 108, which generates a pumping action that can cause the drug compound in the compound chamber 108 to be delivered to the capillaries of the vascular system and thereby enter into the blood stream of the subject. The deflection of the deflectable membrane 106 is directly proportional to the increase of the vapor pressure generated by the phase change of the phase-change fluid in the phase-change fluid chamber 104. For the exemplary embodiment of the micropump 100, a microneedle array 112A may be formed on the bottom portion 110B of the sealing cap layer 110, which is in fluid communication with the compound delivery chamber 111, to provide the desired transdermal delivery.

The at least one through hole 114 in the sealing cap layer 110 may be configured to restrict the flow of compound from the compound chamber 108, thereby providing a coarse flow regulation. The coarse flow regulation provides a coarse control of compound transfer due to variation in temperature and material and manufacturing variations.

An exemplary embodiment of the micropump 100 according to the present disclosure has overall dimensions of 14 mm×14 mm×8 mm. In this embodiment, the radius of the phase-change fluid chamber 104 is 4 mm and the thickness is 2 mm. The radius of the peripheral cavities is 1.5 mm. The deflectable membrane 106 is 140 µm thick. The compound chamber 108 has a radius of 4 mm and a thickness of 2 mm. The dimensions of the micropump 100 are scalable and, depending on a particular application and the volume of the deliverable drug compound, a different device footprint is attainable with ease.

The elements 105, 106, 109, and 110 may be made of composite material, e.g., PDMS (polydimethylsiloxane, made by Dow Corning under the industrial name Sylgard 183). The ratio of silicone present in PDMS to curing agent also present in the PDMS in an exemplary embodiment is 10:1 with curing at 120° C. in a conventional oven for 15 minutes. The resulting Young's Modulus of the PDMS layers occurring for this mix ratio is $7.5 \times 10^5$ Pa.

The micropump 100 does not require special fabrication tools. PDMS is inexpensive and widely available. PDMS requires a low vacuum for removal of air during fabrication and only a conventional oven or a hotplate for curing. The elements 102, 105, 106, 109, and 110 may be bonded to each other by known bonding processes, such as an oxygen plasma process (performed by a Branson™ Asher), which activates the surfaces of the layers. However, other bonding methods are also available, as long as the formed bonds are void free.

Two peripheral cavities (not shown) are formed in the perimeter of the phase-change fluid chamber wall 105 in order to facilitate the injection of a phase-change fluid and venting of air that is present inside the phase-change fluid chamber 104 during the bonding process. These two peripheral cavities (not shown) are formed using stainless-steel cutting tips trimmed to the final sizes with a razor.

Although a variety of phase-change fluids is commercially available, in a liquid phase-change embodiment, the selection of a liquid for the micropump 100 may be based on the boiling point and vapor pressure values of the liquid. In a solid phase-change embodiment, the selection of an appropriate solid material may be based on melting point of the solid and the incompressibility of the material's liquid phase. In a liquid phase-change embodiment, a boiling point slightly above room temperature is desirable, since the temperature rise due to the skin contact is only a few degrees above room temperature. Also, the vapor pressure should be sufficiently large to provide adequate pressure during the delivery of the drug compound to the capillaries of the vascular system to enter into the blood stream of the subject. Two commercial liquids manufactured by 3M™ are found to provide the desired performance. Table 1 shows the boiling point (at 1 atm) and vapor pressure (at 25° C.) for 3M™ FC-3284 (a perfluoro compound) and 3M™ HFE-7000 (methyl perfluoropropyl ether). The same table contains these properties for methanol and isopropanol, which are provided for comparison.

TABLE 1

| Liquid Specifications | | |
|---|---|---|
| Liquid | Boiling Point (1 atm) | Vapor Pressure (25° C.) |
| 3M ™ FC-3284 | 50° C. | 26.77 Torr |
| 3M ™ HFE-7000 | 34° C. | 484.53 Torr |
| Methanol | 64.6° C. | 126.87 Torr |
| Isopropanol | 82.3° C. | 44 Torr |

To demonstrate performance of the micropump 100 using different phase-change fluids, after fabrication and assembly of the phase-change fluid chamber 104, a 5.5 cm capillary tube with an inner diameter of 400 µm is fluidly connected to the compound chamber 108 in order to measure the flow rate and pressure. The compound chamber 108 is filled with dyed deionized water and 10 µL of low boiling point phase-change liquid is injected into the phase-change fluid chamber 104. The two peripheral cavities facilitate injection of the phase-change liquid.

Figure 4:
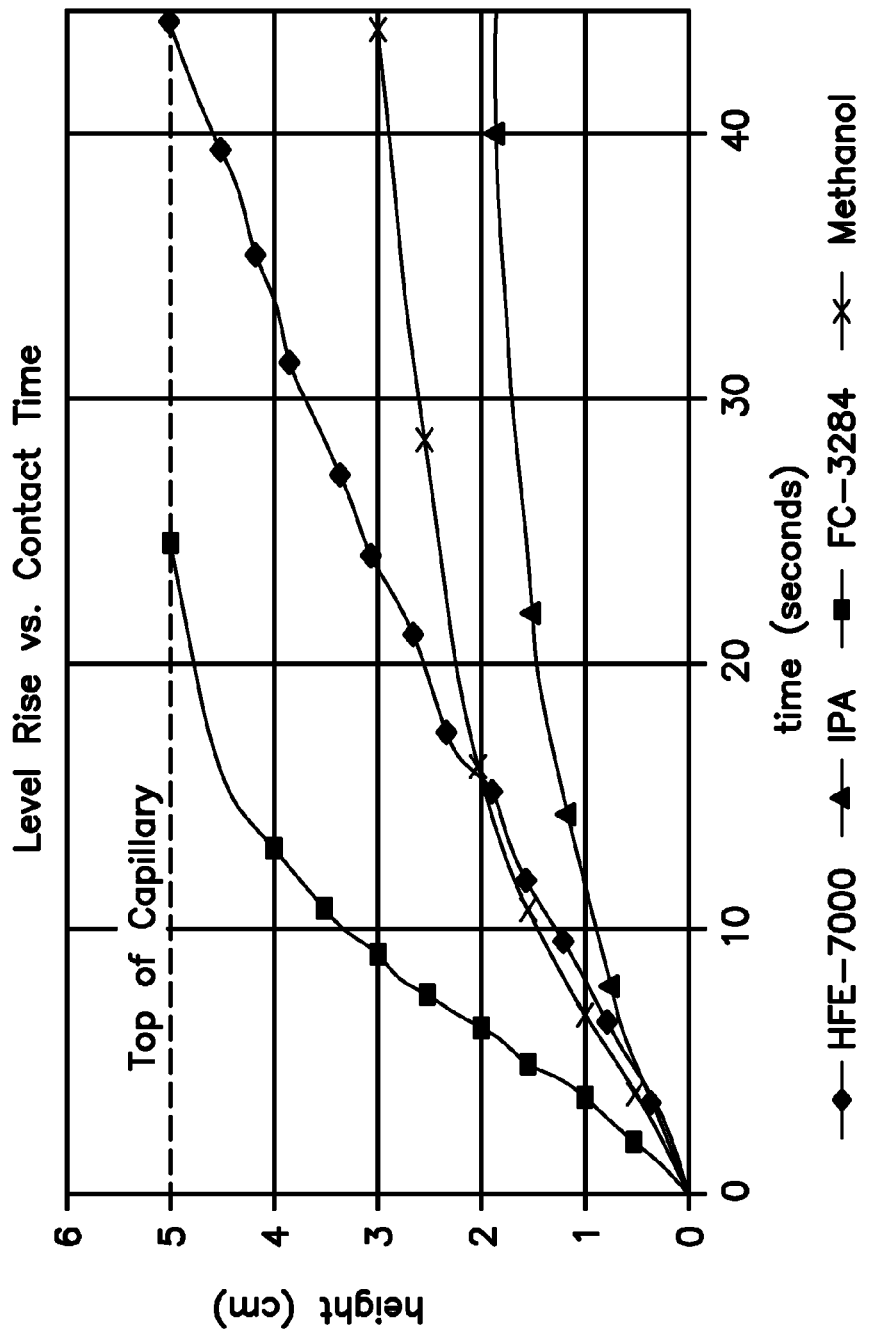
FIG. 4 is a graph of fluid level rise vs. time for different phase-change fluids for the compound delivery micropump device of FIG. 1A.

To test a specific phase-change fluid, the thermally conductive substrate 102 was gently brought into contact with the skin of a subject. FIGS. 3I-3VI depict rise of dyed water in the capillary tube upon skin contact (finger touch for FIGS. 3I-3III and back of hand contact for FIGS. 3IV-3VI). FIG. 4 depicts a graph of the rate at which dyed water rises for various phase-change liquids based on height measured in cm vs. time measured in seconds. HFE-7000 and FC-3284 exhibit flow rates of 33.7 µL/min and 60.1 µL/min and back-pressures (i.e., pressures applied at the open end of the capillary tube) of 4.87 psi and 2.24 psi, respectively. HFE-7000 was found to exhibit slower flow rate than the FC-3284 partially due to absorption in PDMS, which leads to swelling of the cavity sidewalls, membrane stretching, and lower pressure in the compound chamber 108. Analogous swelling occurred during the injection of isopropanol.

Figure 5:
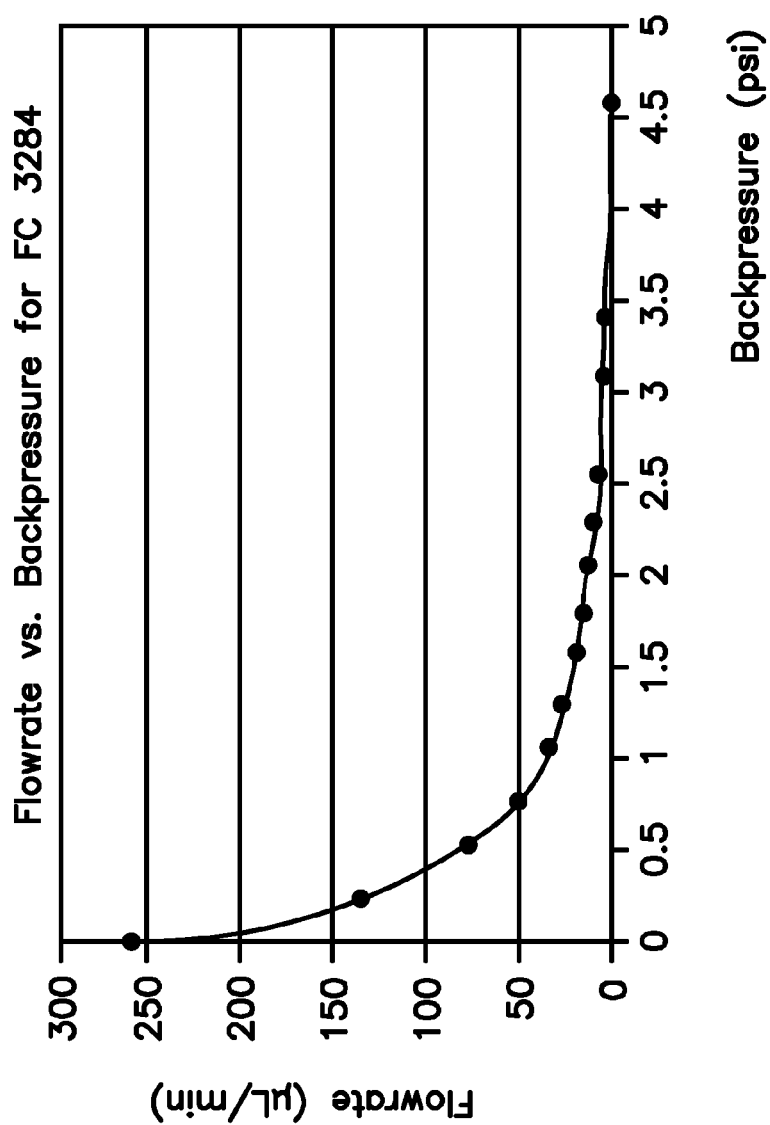
FIG. 5 is a graph of flow rate vs. backpressure for one of the phase-change fluids of FIG. 4.

Referring to FIG. 5, the flow rate versus backpressure is plotted for FC-3284 as the phase-change liquid. A hotplate set to 31° C. is used for testing in order to achieve controlled heating. The test setup includes a pressure regulator (Porter Instrument Company Inc., Hatfield, Pa., USA) with the inlet connected to nitrogen gas supply and the outlet connected to a digital pressure gauge (Omega Engineering Inc., Stamford, Conn., USA) and the capillary tube.

Initially, the flow rate is measured at atmospheric backpressure, i.e., the capillary end is open to the atmosphere. The atmospheric backpressure flow rate is calculated to be 260 µL/min. This value is larger than the one calculated with thermal conduction due to finger contact. This difference is the result of heating with the hotplate surface, which causes the entire backside area of the micropump to be rapidly and uniformly heated to 31° C. as compared to the near-linear and localized temperature increase due to finger contact.

As shown in FIG. 5, an exponential decrease of the flow rate is observed with the increase of backpressure. The flow rate decreases exponentially while the applied backpressure increases to a plateau backpressure of 4.46 psi. The maximum backpressure when the micropump 100 is heated with a hotplate is 4.46 psi. The same test setup is also used to measure the maximum backpressure when pumping with finger touch. The plateau value for finger contact is 4.19 psi.

While the aforementioned structure is preferably suitable for a quick delivery of a drug compound into the capillaries of the vascular system to enter into the blood stream of a subject, another embodiment of a transdermal drug compound delivery micropump device may be configurable to deliver the desired compound over an extended period of time.

Figure 6:
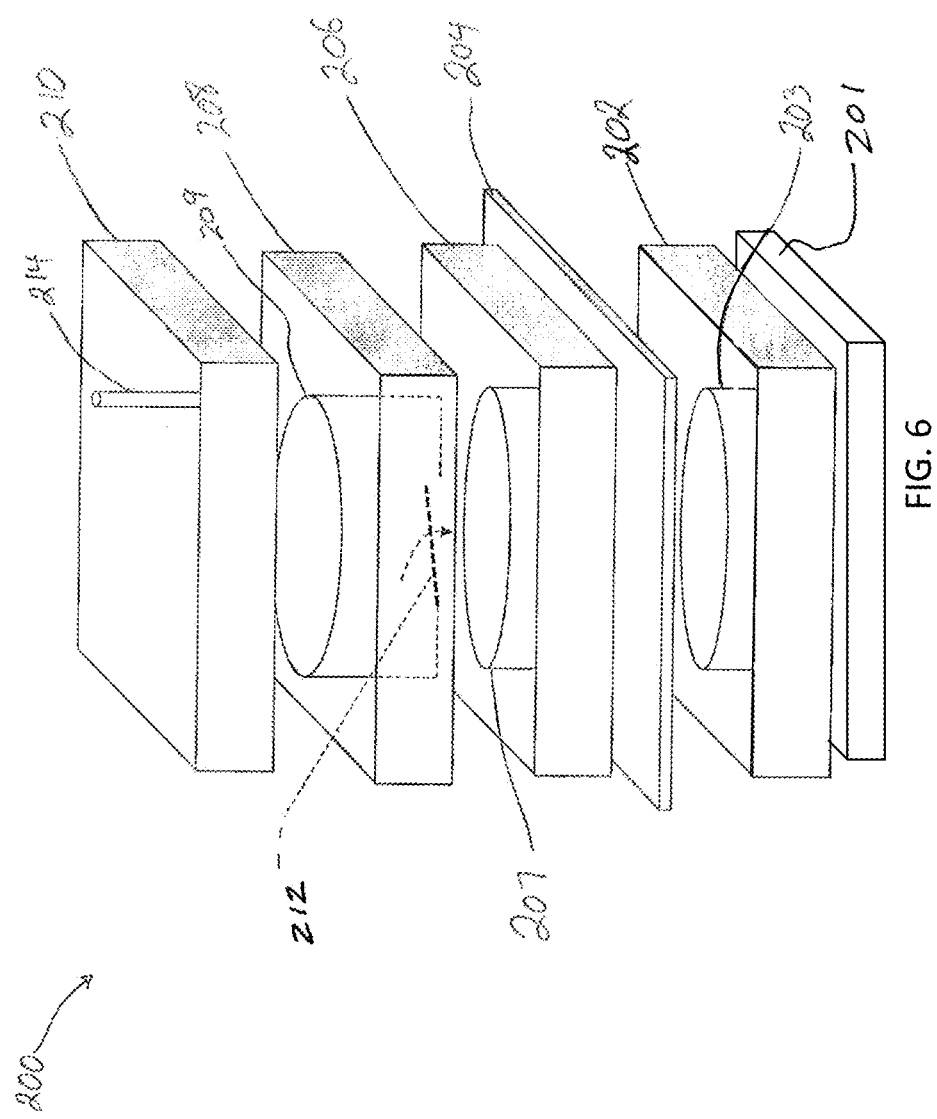
FIG. 6 is a perspective exploded view of the layers forming the transdermal drug compound delivery micropump device of FIG. 1A with various layers according to one embodiment of the present disclosure.

Referring to FIG. 6, an exploded perspective view of a two-stage transdermal drug compound delivery micropump device 200 according to the present disclosure is depicted. The micropump 200 includes and is defined by a phase-change fluid chamber 203, a primary compound chamber 207, and a secondary compound chamber 209. The phase-change fluid chamber 203 is defined by a cylindrical phase-change fluid chamber wall 202, a thermally conductive substrate 201 on one side, and a deflectable membrane 204 on the opposing side. The phase-change fluid chamber 203 is configured to store a material that readily and substantially changes volume in response to heat. Such a material may be a phase-change fluid, which changes phase (e.g., evaporates) within the temperature range between slightly below room temperature and the surface temperature of a subject's skin.

The thermally conductive substrate 201 may be made of a highly, thermally conductive material, such as silicon. Metallic substrates (e.g., copper, gold, and other substrate materials often found in microfabrication processes) may also be used as long as the thermally conductive substrate 201 is biocompatible and compatible with the other materials in the device, including the drug compound to be administered.

The deflectable membrane 204 is in contact with the phase-change fluid chamber 203 and the primary compound chamber 207 and is configured to deflect when the material inside the phase-change fluid chamber 203 changes phase, thereby exerting pressure on the deflectable membrane 204.

The primary compound chamber 207 includes and is defined by a cylindrical primary compound chamber wall 206, a one-way valve 212 on one side, and the deflectable membrane 204 on the opposing side. The primary compound chamber 207 is configured to store a first portion of the total volume of a drug compound that is to be delivered through the micropump 200. The one-way valve 212 is configured to enable fluid transfer from the primary compound chamber layer 206 to the secondary compound chamber layer 208 but not vice versa.

The secondary compound chamber 209 includes and is defined by a cylindrical secondary compound chamber wall 208, the one-way valve 212 on one side and a sealing cap 210 on the opposing side. The secondary compound chamber 209 is configured to store a second portion of the total volume of a drug compound that is to be delivered through the micropump 200. The primary 207 and secondary 209 compound chambers are isolated from each other by the one-way valve 212.

The sealing cap layer 210 is configured to seal with the secondary compound chamber 209 and includes a through hole 214 formed in the sealing cap layer 210 that provides a flow channel between the secondary compound chamber 209 and the capillaries of the vascular system through a needle (not shown) or an needle array (not shown) and thereby the blood stream of the subject. The elements 202, 204, 206, 208 and 210 may be made of composite material, e.g., PDMS.

In operation, once skin contact is made with the thermally conductive substrate 201, the material in the phase-change fluid chamber 203 changes phase and thereby increases its volume. The deflectable membrane 204 deflects in response to the increase in the pressure of the phase-change fluid chamber 203. The deflection of the deflectable membrane 204 forces a volume of drug compound in the primary compound chamber 207 into the secondary compound chamber 209 through the one-way valve 212, thereby increasing the pressure within secondary compound chamber 209. The increased pressure in the secondary compound chamber 209 forces a combined volume of drug compound into the capillaries of the vascular system and thereby the blood stream of the subject via the through hole 214 and the needle (not shown).

In the deflected state, the pressure in the primary compound chamber 203 is substantially the same as the pressure within the secondary compound chamber 209. When skin contact is removed and the phase-change fluid reverses its phase change, the deflectable membrane layer 204 returns to its non-deflected state, which causes the primary compound chamber layer 203 to also return substantially to its original shape. In the non-deflected state, however, the secondary compound chamber 209 retains its higher pressure due to the closure of the one-way valve 212. The secondary compound chamber 209 may be configured to have a pliable material that allows pressurization of an incompressible fluid within it. The drug compound in the secondary compound chamber 209 is then allowed to be released in a controlled manner through the through hole 214 for a period of time after skin contact is removed.

Figure 7:
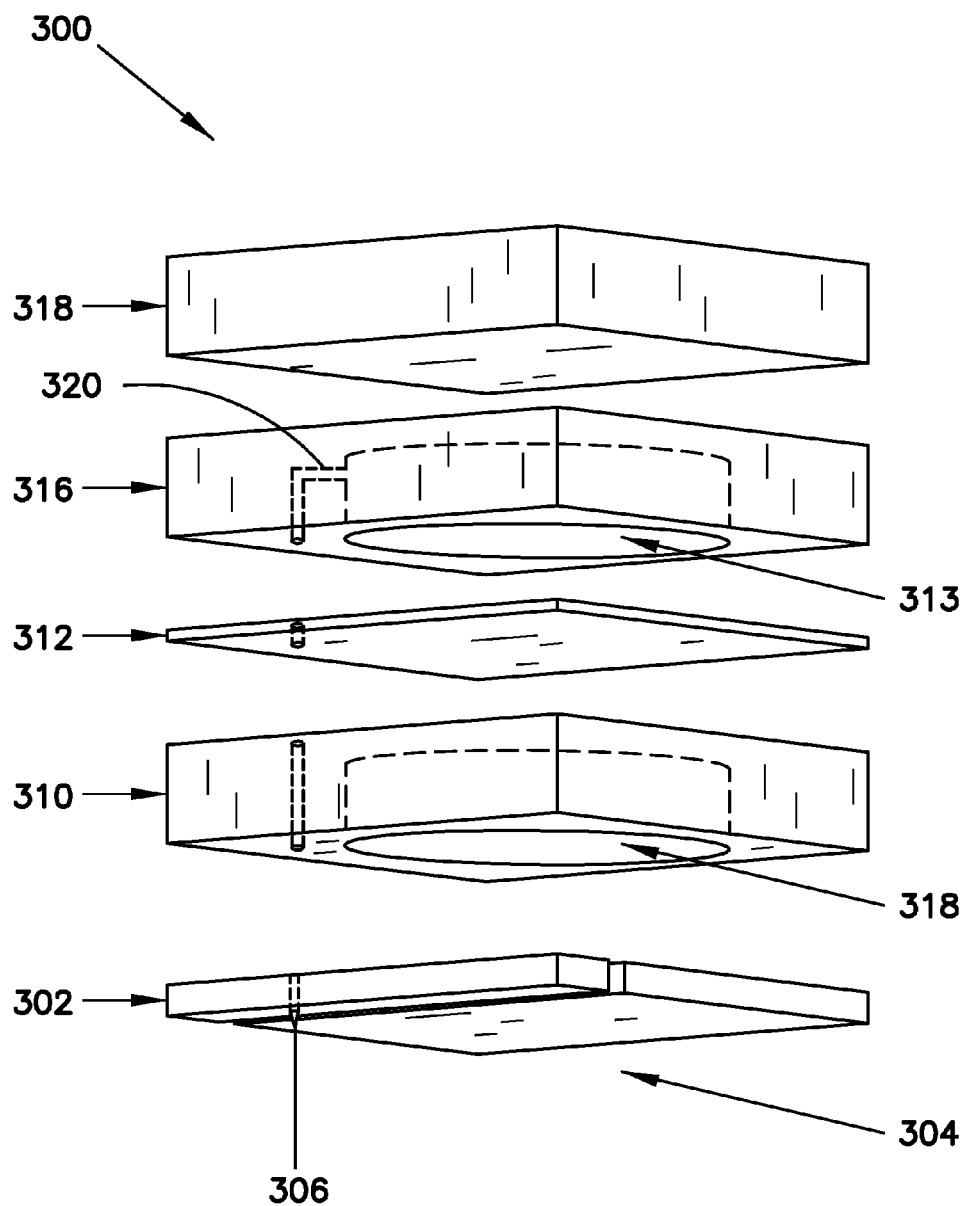
FIGS. 7 and 8 depict an exploded view and a side view of an embodiment of a transdermal drug compound delivery micropump according to the present disclosure.
Figure 8:
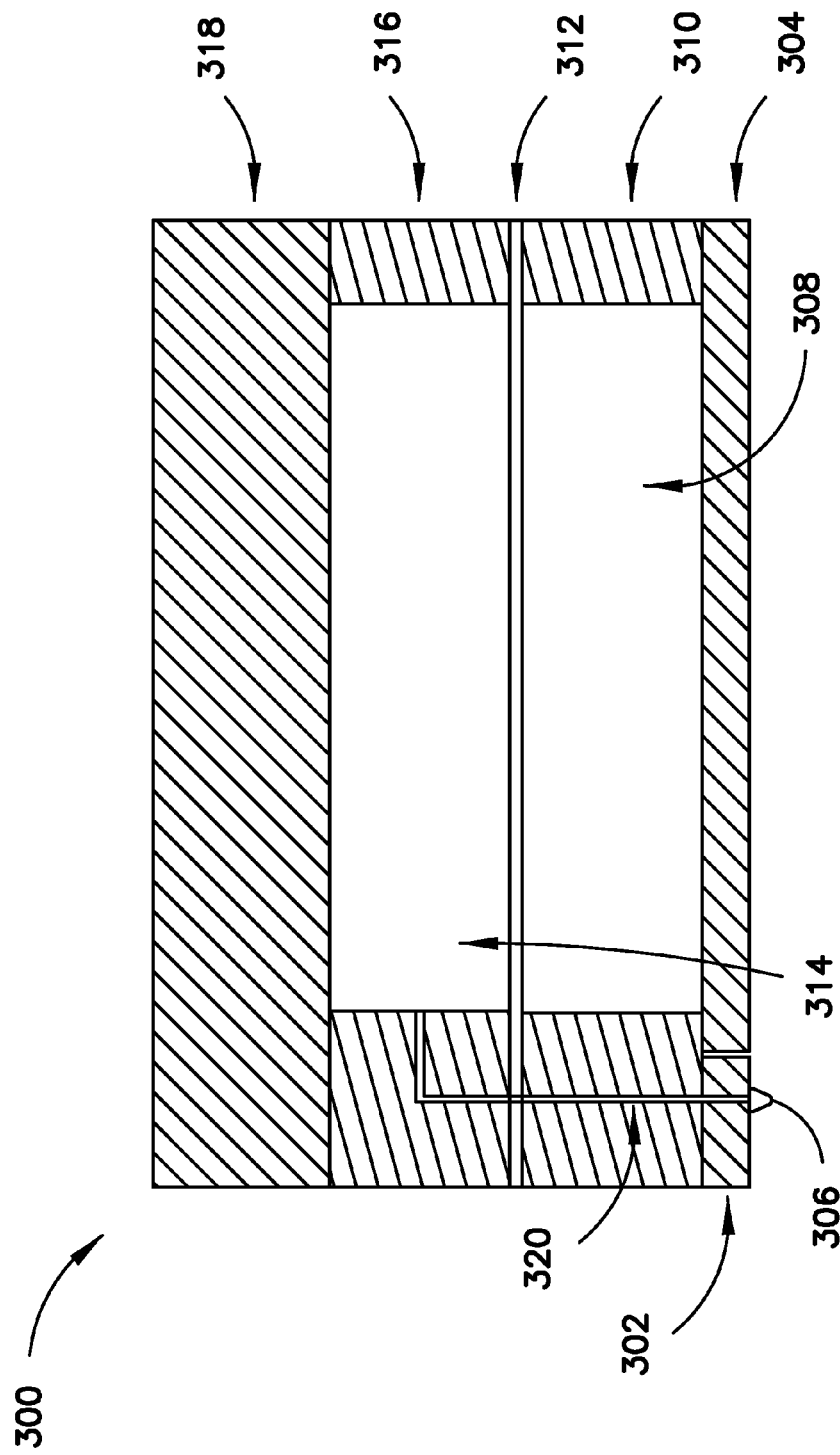

Referring to FIGS. 7 and 8, an exploded view and a side view of another embodiment of a transdermal drug compound delivery micropump device 300 according to the present disclosure is provided. The micropump 300 includes a needle substrate 302, a thermally conductive substrate 304, at least one needle 306, a first chamber 308, a first wall 310, a deflectable membrane layer 312, a second chamber 314, a second wall 316, a cover 318, and a channel 320. The needle substrate 302 is adjacent to the thermally conductive substrate 304 and is configured to include at least one needle 306 or an array of needles (not shown). The thermally conductive substrate 304 is made of a material suitable for efficient transfer of heat from a heat source, such as the skin of a subject.

On one side, interior space of the chamber 308 is in contact with the thermally conductive substrate 304. The chamber 308 is enclosed by the wall 310. The wall 310 is rigid and may be made from PDMS. On another side, the interior space of the chamber 308 is in contact with the deflectable layer 312, which may be made from a thin layer of PDMS. Furthermore, on one side, internal space of the chamber 314 is in contact with the deflectable layer 312. The chamber 314 is enclosed by the wall 316. The wall 316 is rigid and may be made from PDMS. On another side, the interior space of the chamber 314 is capped by the rigid cover 318, made from PDMS, glass, or other suitably rigid material. The chamber 314 is configured to store a drug compound to be injected into the vascular system of a subject. The channel 320 is continuously formed in the walls 316 and 310, the deflectable layer 312, and the needle substrate 302 and enables fluid communication between the interior space of the chamber 314 and the at least one needle 306.

The chamber 308 is configured to store a material that readily and substantially changes volume in response to heat. The material in the chamber 308 is exposed to heat by a subject touching the thermally conductive substrate 304, which transfers heat from the skin of the subject to the material in the chamber 308 and increases the volume of the material, thereby increasing the pressure in the chamber 308. The increased pressure in the chamber 308 is transferred to the chamber 314 by deflection of the deflectable layer 312. The increased pressure in the chamber 314 forces the compound therein into the channel 320 and out the at least one needle 306.

In one embodiment according of the present disclosure, a mixture of yeast, water, and sucrose can be used as the actuation material (i.e., the material in the chamber 308). This actuation fluid yields a compound flow rate that is considerably slower than when the actuation material is a phase-change material. When stored at low temperatures (e.g., less than 5° C.), the yeast cells remain dormant, and thus no increase in volume in the mixture 308 is realized. Therefore, the drug compound in the chamber 314 is not pumped through the channel 320. However, upon contact of the thermally conductive substrate 304 with the skin, the skin surface temperature being about 32° C., causes heat from the skin to activate the yeast cells, triggering these cells to begin a fermentation process of the sucrose into ethanol and carbon dioxide gas ($CO_2$). The fermentation process initially provides a conversion to glucose and fructose by an invertase enzyme, which generates $CO_2$ gas and increases the pressure in the chamber 308. As a result, the deflectable layer 312 deflects and thereby forces the drug compound present in the chamber 314 through the channel 320. The concentration of sucrose and yeast cells in the chamber 308 is low enough that the fermentation process produces $CO_2$ at a slow rate, which causes only a slow displacement of the compound from the chamber 314. The slow displacement of the compound from the chamber 314 advantageously provides a transdermal micropump for delivering drug compounds suitable for the injection of small doses over a period of hours, rather than seconds.

Figure 9:
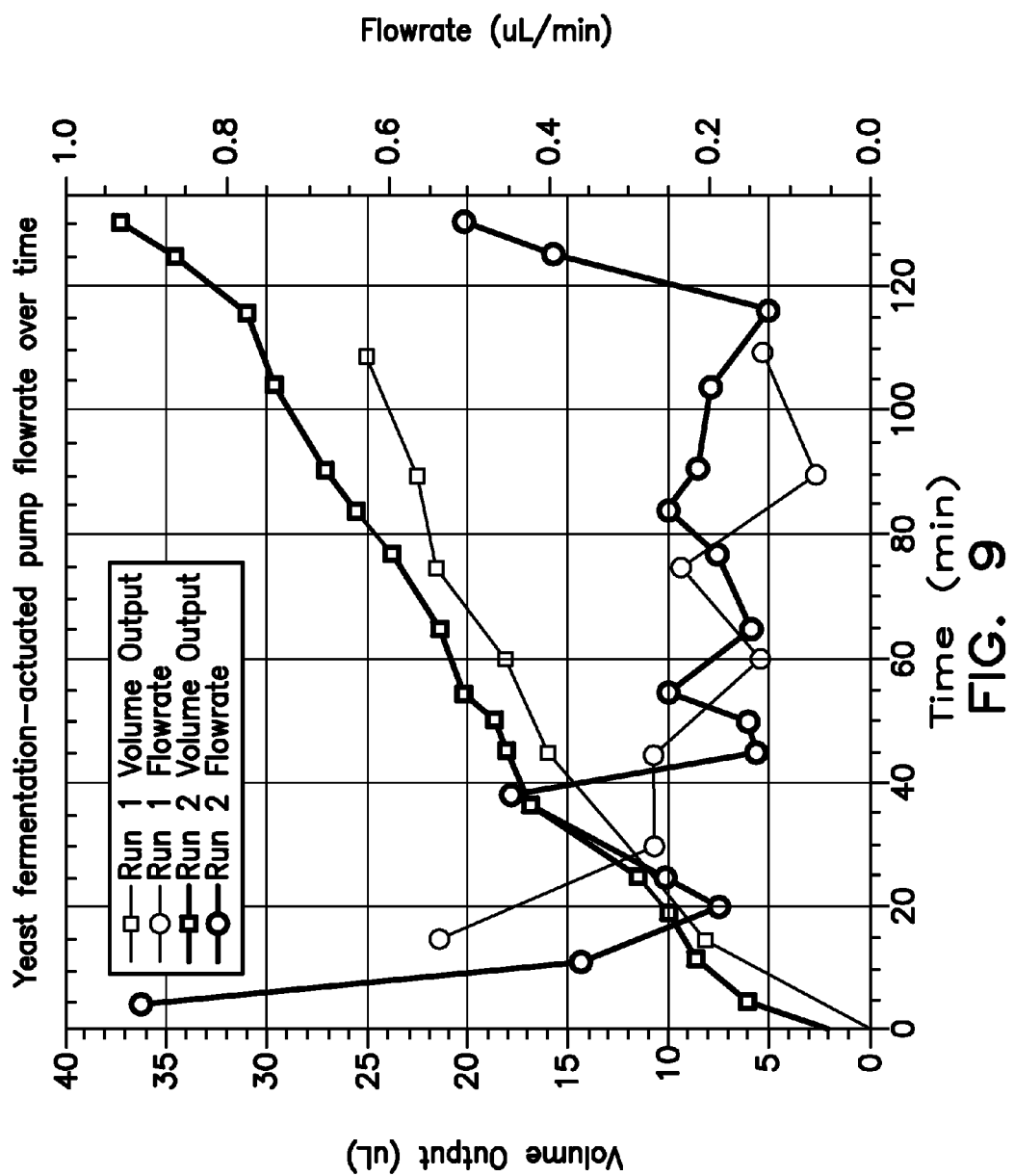
FIG. 9 depicts a graph of displaced volumes of a compound, measured in micro liters (μL) vs. time, measured in minutes (min), and flow rate of a compound, measured in micro liters per minute (μL/min) vs. time, measured in minutes (min), for two test runs for the transdermal micropump of FIGS. 7 and 8.

One embodiment of a transdermal micropump 300 according to the present disclosure was demonstrated using *S. cerevisiae* yeast (commonly used for making bread and beer). One can appreciate that other yeast species may be used if different storage or delivery temperatures are desired. FIG. 9 depicts a graph of displaced volumes (μL) of a compound versus time (min) and flow rate (μL/min) versus time (min) for two test runs (test runs 1 and 2), wherein the test run 1 was performed immediately after preparing the yeast solution and the test run 2 was performed after storing the prepared yeast solution at 0.6° C. for 36 hours. The test results show an average flow rate of less than 0.3 μL/min for both test runs, a value much lower than 60 μL/min achieved using the perfluoro phase-change compound of a different embodiment as the actuation material. Additionally, the volume output versus time does not vary significantly between the two trials, suggesting that the performance of the yeast mixture is not affected by preparation and storage prior to use, as would be expected from yeast that remains dormant during storage. The flow rate of the drug compound may be modified by altering the yeast and sucrose amounts or concentrations.

Figure 10:
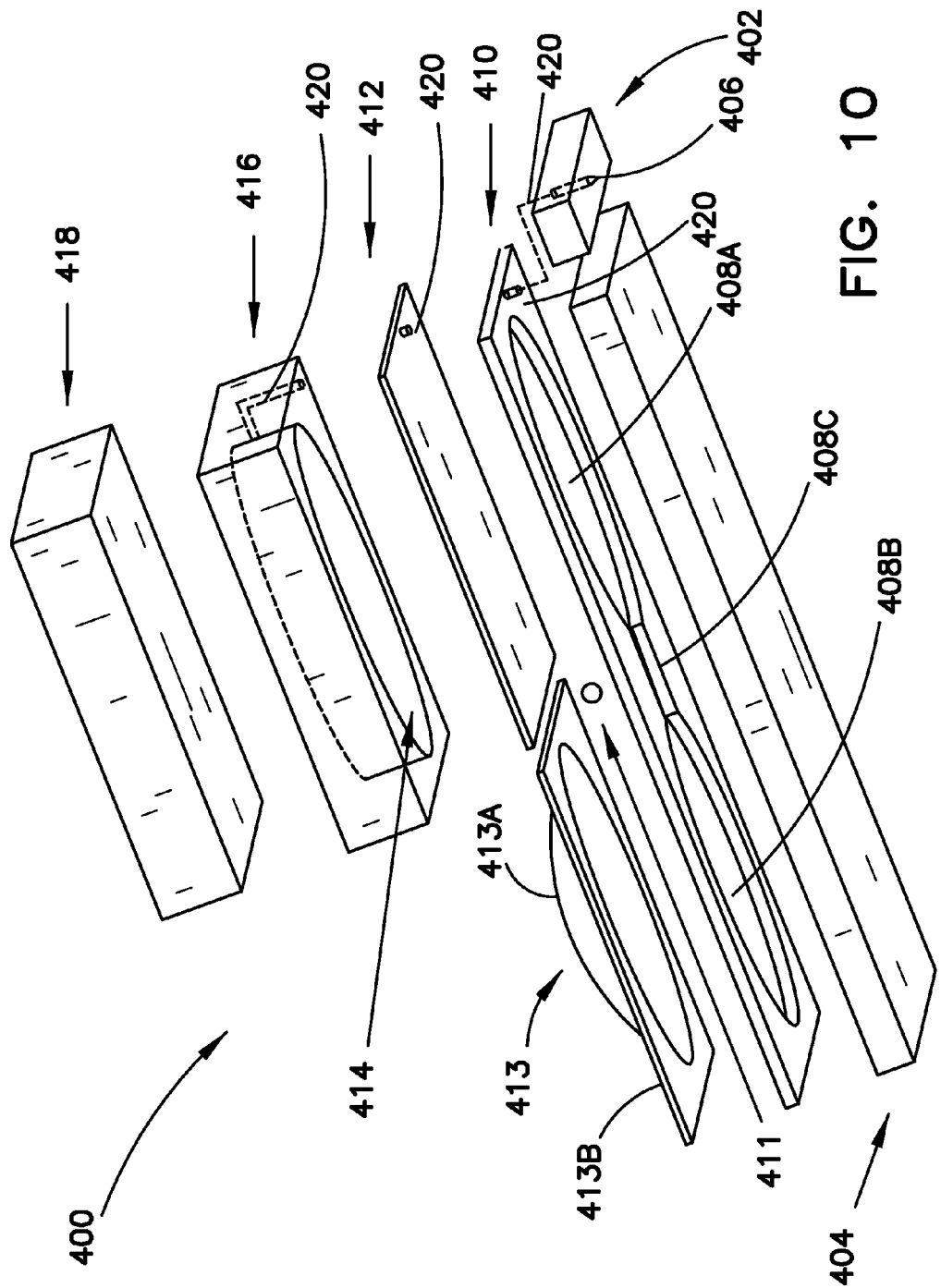
FIGS. 10 and 11 depict an exploded view and a side view of another embodiment of a transdermal micropump according to the present disclosure.
Figure 11:
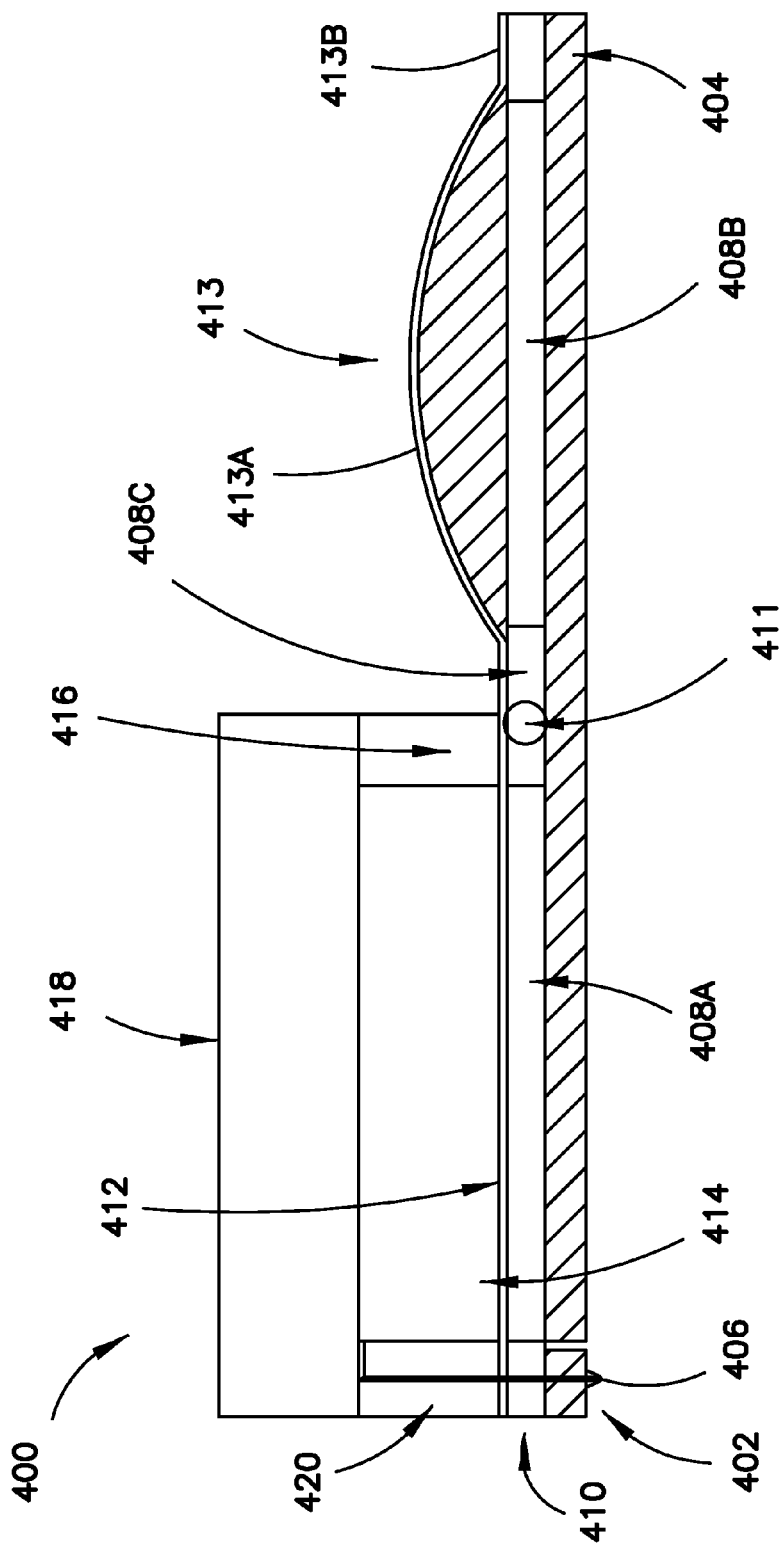

While the results presented in FIG. 9 demonstrate a long shelf life is possible for a previously-prepared yeast mixture used in the micropump 300 which is stored at a cold temperature, it is advantageous to maintain the yeast in a dry form and prepare it when the transdermal micropump is needed, thereby eliminating the requirement to store the micropump at a cold temperature. Referring to FIGS. 10 and 11, an exploded view and a side view of an embodiment of a transdermal drug compound delivery micropump device according to the present disclosure are shown.

The micropump 400 includes a needle substrate 402 constructed to include at least one needle 406, a thermally conductive substrate 404, a first chamber 408A, a second chamber 408B, a first wall 410, a deflectable layer 412, a microchannel 408C, a blocking member 411, a dimple assembly 413, a compound chamber 414, a second wall 416, a sealing cap 418, and a channel 420. The needle substrate 402, which is comprised of at least one needle 406 or an array of needles (not shown), is positioned adjacent to the thermally conductive substrate 404. The thermally conductive substrate 404 is of a material suitable for efficient transfer of heat from a heat source, e.g., skin of a subject.

On one side, the interior spaces of the chambers 408A and 408B are in contact with the thermally conductive substrate 404. The chambers 408A and 408B are enclosed by the wall 410. The wall 410 is rigid and may be made from PDMS. On another side the interior space of the chamber 408A is in contact with the deflectable layer 412, which may be made from a thin layer of PDMS. The chambers 408A and 408B are connected via the microchannel 408C. The blocking member 411 (e.g., a wax ball) is initially disposed in the microchannel 408C to prevent flow of material between the chambers 408A and 408B. The interior space of the chamber 408B is in contact with the dimple assembly 413, formed of a permanently deformable member 413A that is initially in the shape of a dome connected to a flat member 413B, which is positioned on top of the chamber 408B. The deformable member 413A is connected to the flat member 413B which is positioned on top of the chamber 408B. The deformable member 413A and the flat member 413B can be integrally formed as a pre-manufactured component.

On one side, the interior space of the compound chamber 414 is in contact with the deflectable layer 412. The compound chamber 414 is enclosed by the wall 416. The wall 416 is rigid and can be made from PDMS. On another side, the interior space of the compound chamber 414 is covered by the rigid sealing cap 418. The sealing cap 418 may be made from PDMS, glass, or other suitably rigid material. The compound chamber 414 is configured to store a drug compound to be injected into the vascular system of a subject. The channel 420 is formed through the walls 416 and 410, the deflectable layer 412, and the needle substrate 402 and enables fluid communication between the interior space of the compound chamber 414 and the needle 406.

The chamber 408A contains a reactive material that, upon being combined with an activating agent, forms a combined mixture that readily and substantially increases in volume when exposed to heat. The chamber 408B contains an activating agent, such as water, which is separated from the chamber 408A by the blocking member 411. The activating agent in the chamber 408B is in contact with the air space under the dome-shaped deformable member 413A and is therefore positioned between the blocking member 411, the deformable member 413A, and the flat member 413B.

When the micropump 400 is used, the subject presses on the deformable member 413A causing the activating agent in the chamber 408B to force the blocking member 411 in the microchannel 408C into the chamber 408A. With the blocking member 411 displaced, the activating agent in the chamber 408B moves into the chamber 408A, which initially holds the reactive material, such as a dry mixture of yeast and sucrose. The chamber 408A can be configured such that the reactive material lines the interior of the chamber 408A. The combined mixture of the activating agent and the reactive material is exposed to heat when a subject touches the thermally conductive substrate 404 or places it on a skin surface, which transfers heat from the skin of the subject to the mixture in the chamber 408A.

In one embodiment according to the present disclosure, the dry yeast mixture remains inactive at room temperature prior to mixing with water and, therefore, does not require refrigeration. The combination of water and the dry yeast mixture is ready for the fermentation process similar to the micropump 300. The fermentation process occurs once the subject touches the thermally conductive substrate 404. The reader should appreciate that once the deformable member 413A is deformed, it retains its deformed shape, thereby preventing the combined mixture from being sucked out of the chamber 408A.

Upon exposure of the combined mixture in the chamber 408A to heat, the volume of the mixture increases, thereby pushing on the deflectable layer 412, which pressurizes the compound chamber 414. The drug compound in the compound chamber 414 is thereby forced out of the compound chamber 414 into the channel 420 and through the needle 406. Airspace may be provided at the top of the compound chamber 414 in the form of a bubble. In which case air is initially displaced out of the device through the needle 406. Thereafter, the subject can place the transdermal pump 400 on the skin to receive the drug compound in the compound chamber 414.

In an alternative embodiment according to the present disclosure, the dimple assembly 413 can be replaced by a simple cap made from PDMS, glass, or the like, and the blocking member 411 replaced by a low melting point material (preferably a hydrophobic material) that, when in room temperature, prevents transfer of activating agent from the chamber 408B to the chamber 408A. By placing the micropump 400 of this alternative embodiment on the skin of the subject, heat from the skin is transferred to the blocking member 411 causing the blocking member to melt. The melting of the blocking member 411 enables transfer of activating agent from chamber 408B to chamber 408A and process proceeds as described.

In another embodiment according to the present disclosure, a valve scheme can be incorporated with the chamber 408A such that when activating agent from the chamber 408B migrates to the chamber 408A, air in the chamber 408A is initially allowed to exit from the chamber 408A. However, the valve scheme is configured to prevent the $CO_2$ gas that is generated during the fermentation process from escaping.

Figure 12:
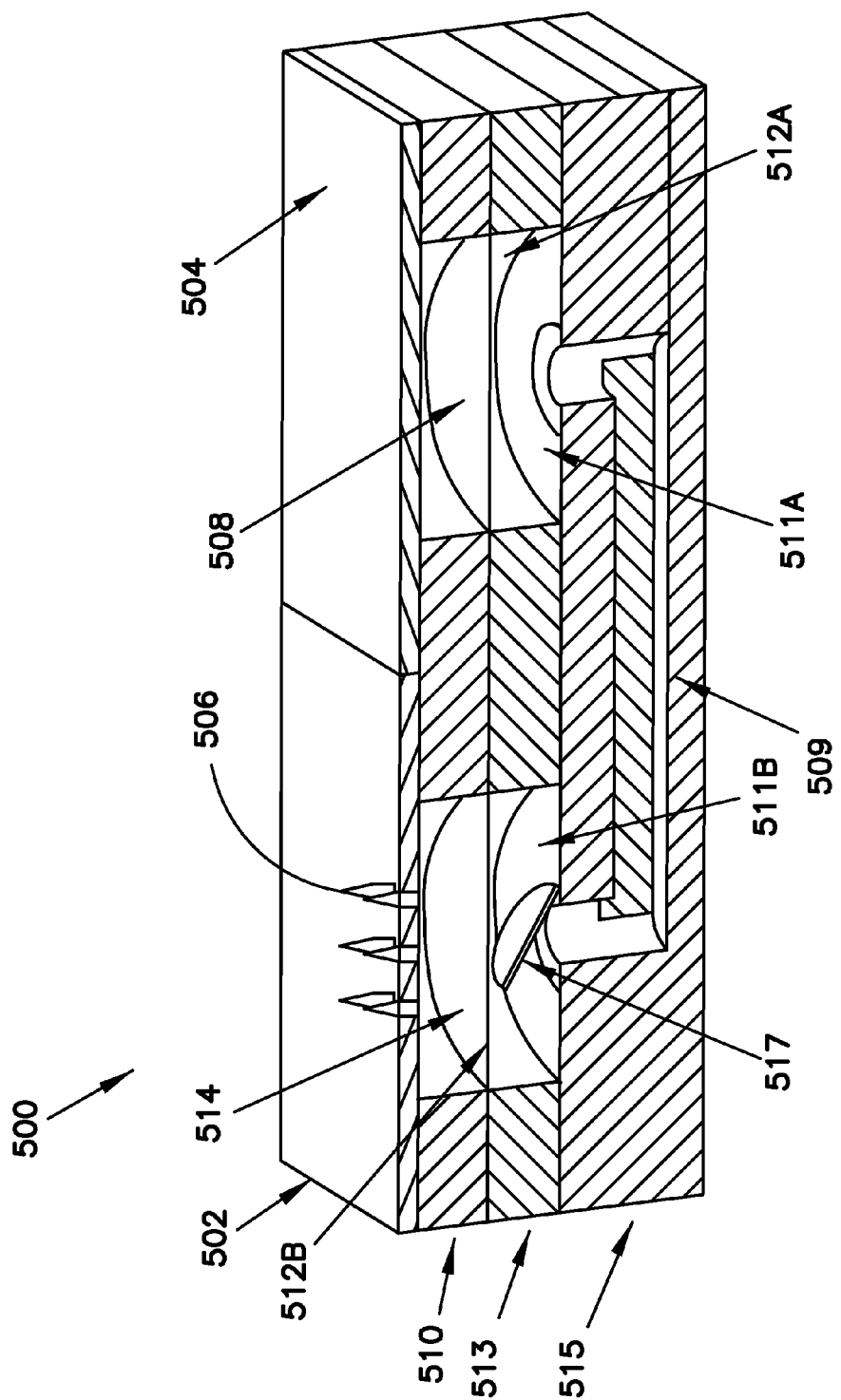
FIGS. 12 and 13 depict an exploded view and a side view of another embodiment of a transdermal micropump according to the present disclosure.
Figure 13:
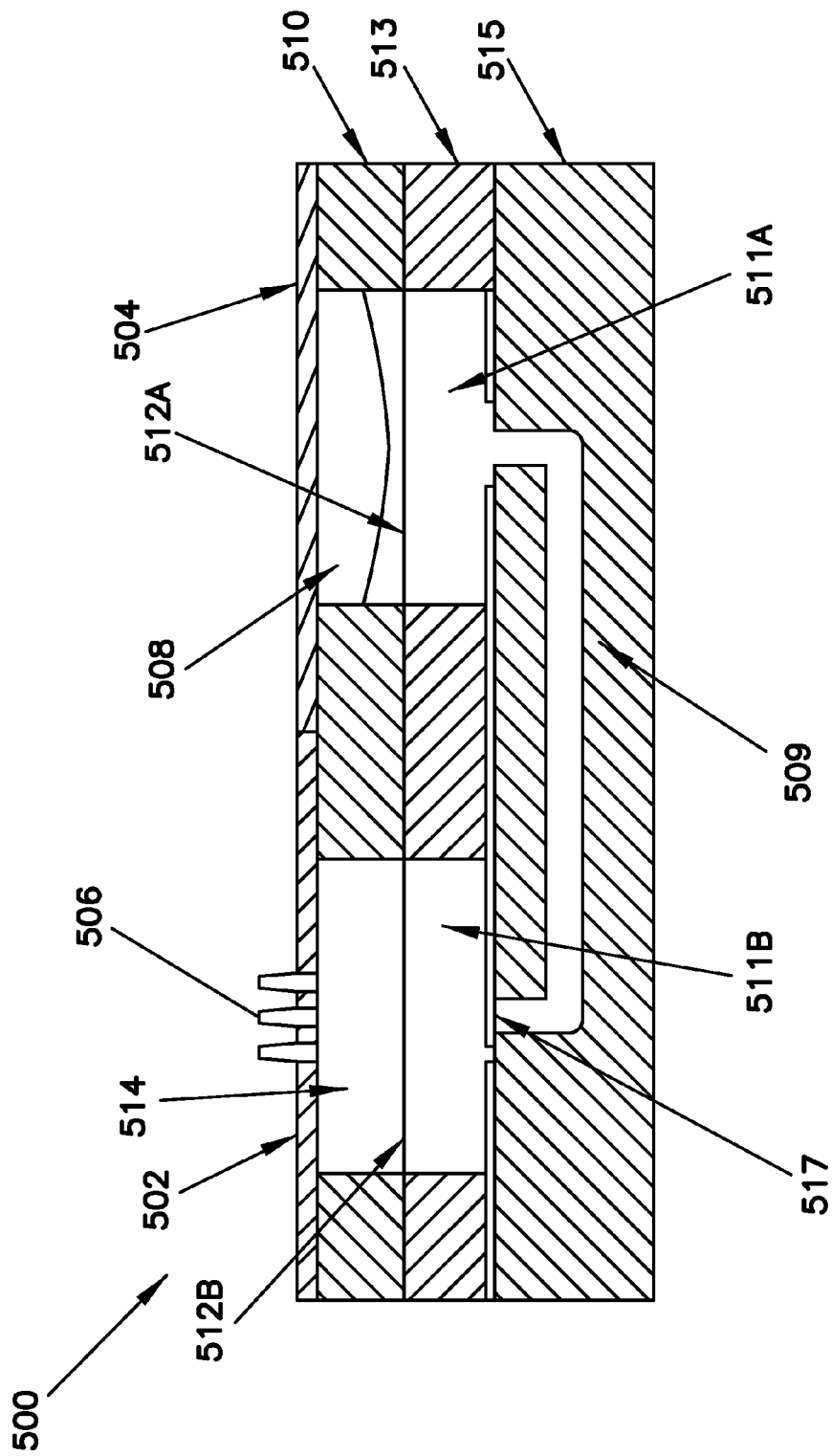
Figure 14A:
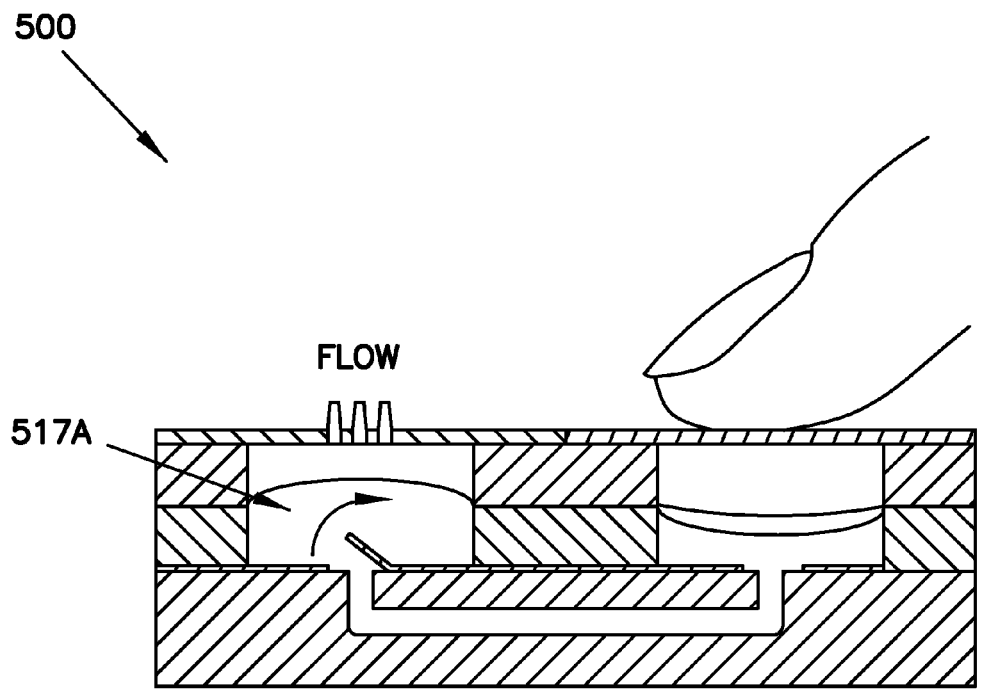
FIGS. 14A and 14B depict the transdermal micropump of FIGS. 12 and 13 in various operational positions.
Figure 14B:
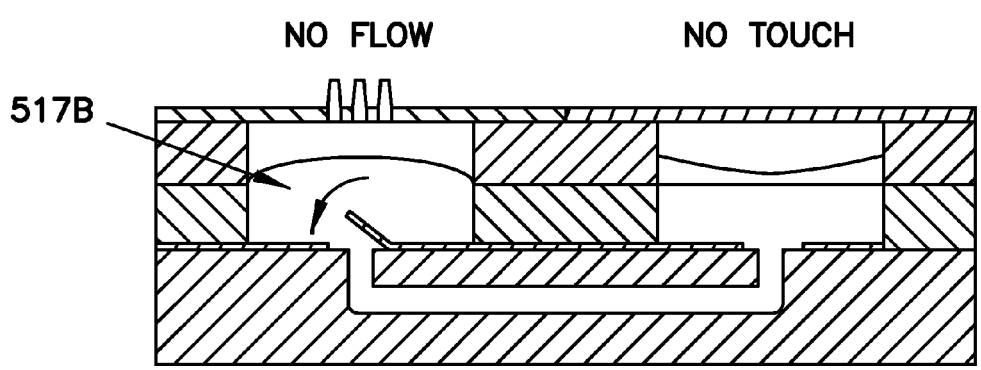

While the previously disclosed embodiments according to the present disclosure are suitable for injecting a drug compound in a continuous manner, it is also advantageous to provide a multi-dose transdermal micropump that is capable of providing multiple doses. FIGS. 12 and 13 depict an embodiment of a transdermal drug compound delivery micropump device 500 capable of providing multiple doses of a drug compound to a subject. FIGS. 14A and 14B depict the micropump 500 in various operational positions.

The micropump 500 includes a needle substrate 502, a thermally conductive substrate 504, a first chamber 508, a first wall 510, a second chamber 511A, a second wall 513, a deflectable layer 512A, a microchannel 509, a third wall 515, a one-way valve 517, a third chamber 511B, a deflectable layer 512B, and a compound chamber 514.

The needle substrate 502 is comprised of at least one needle or an array of needles 506 and is disposed adjacent to the thermally conductive substrate 504. The thermally conductive substrate 504 is of a material suitable for efficient transfer of heat from a heat source, e.g., skin of a subject. On one side, interior space of the chamber 508 is in contact with the thermally conductive substrate 504. The chamber 508 is enclosed by the wall 510. The wall 510 is rigid and may be made from PDMS. On another side, the interior space of the chamber 508 is in communication with interior space of the chamber 511A, which is enclosed by the wall 513. The chambers 508 and 511A are separated by the deflectable layer 512A, which may be made from a thin layer of PDMS. The wall 513 is rigid and may be made from PDMS. The chamber 511A is in fluid communication with the microchannel 509, which is enclosed by the wall 515. The wall 515 is rigid and may be made of PDMS. The microchannel 509 fluidly connects the chamber 511A with the chamber 511B via the one-way valve 517. The chamber 511B is enclosed by the wall 513. The one-way valve 517 may be made from a thin film and may be positioned at the bottom of the chamber 511B.

The interior space of the chamber 511B is in contact with the deflectable layer 512B, which may be made from a thin layer of PDMS. The deflectable layer 512B is in contact with the compound chamber 514, which is enclosed by the rigid wall 510 and capped by the needle substrate 502. The compound chamber 514 is thereby in fluid communication with the at least one needle or needle array 506. FIGS. 14A and 14B depict various operational positions of the one-way valve 517, which is shown in an opening position 517A and a closing position 517B.

The chamber 508 is configured to store a material that readily and substantially changes volume in response to heat, such as a phase-change material that changes phase (e.g., from a liquid to a gas) due to transferred heat. The material in chamber 508 is exposed to heat by a subject touching the thermally conductive substrate 504, which transfers heat from the skin of the subject to the material. The chambers 511A and 511B contain a fluid, such as air. Because of the one-way valve 517, the fluid in these chambers can freely move from the chamber 511A to the chamber 511B, but the reverse flow of fluid from the chamber 511B to the chamber 511A is prevented by the one-way valve 517. The compound chamber 514 is filled with a drug compound to be injected into the vascular system of the subject.

When the micropump 500 is used, the subject touches the thermally conductive substrate 504, which causes the volume of the material in the chamber 508 to increase. The increased volume deflects the deflectable layer 512A, which deflects into the interior chamber of the chamber 511A. As a result, fluid is forced out of the chamber 511A and into the chamber 511B through the microchannel 509 and through the one-way valve 517. The transfer of fluid pressurizes the fluid in the chamber 511B and causes the deflectable layer 512B to deflect into the compound chamber 514. This deflection forces the drug compound out of the compound chamber 514 through the needle array 506. Transfer of the compound can result in a small reduction of the pressure within the chambers 511A and 511B. Therefore, a continued increase of pressure in these chambers is needed for the compound to be pumped continuously.

When the subject ceases to apply heat to the thermally conductive substrate 504, the volume of the material in the chamber 508 decreases due to, for example, a reversal of the prior phase change. This decrease results in a reduction of the deflection of the deflectable layer 512A into the chamber 511A, which generates a tendency for a reverse flow of air from the chamber 511B to 511A. However, the one-way valve 517 prevents such a reverse flow. As a result, pressure within the compound chamber 514 reaches equilibrium, and no additional compound is pumped.

Figure 15:
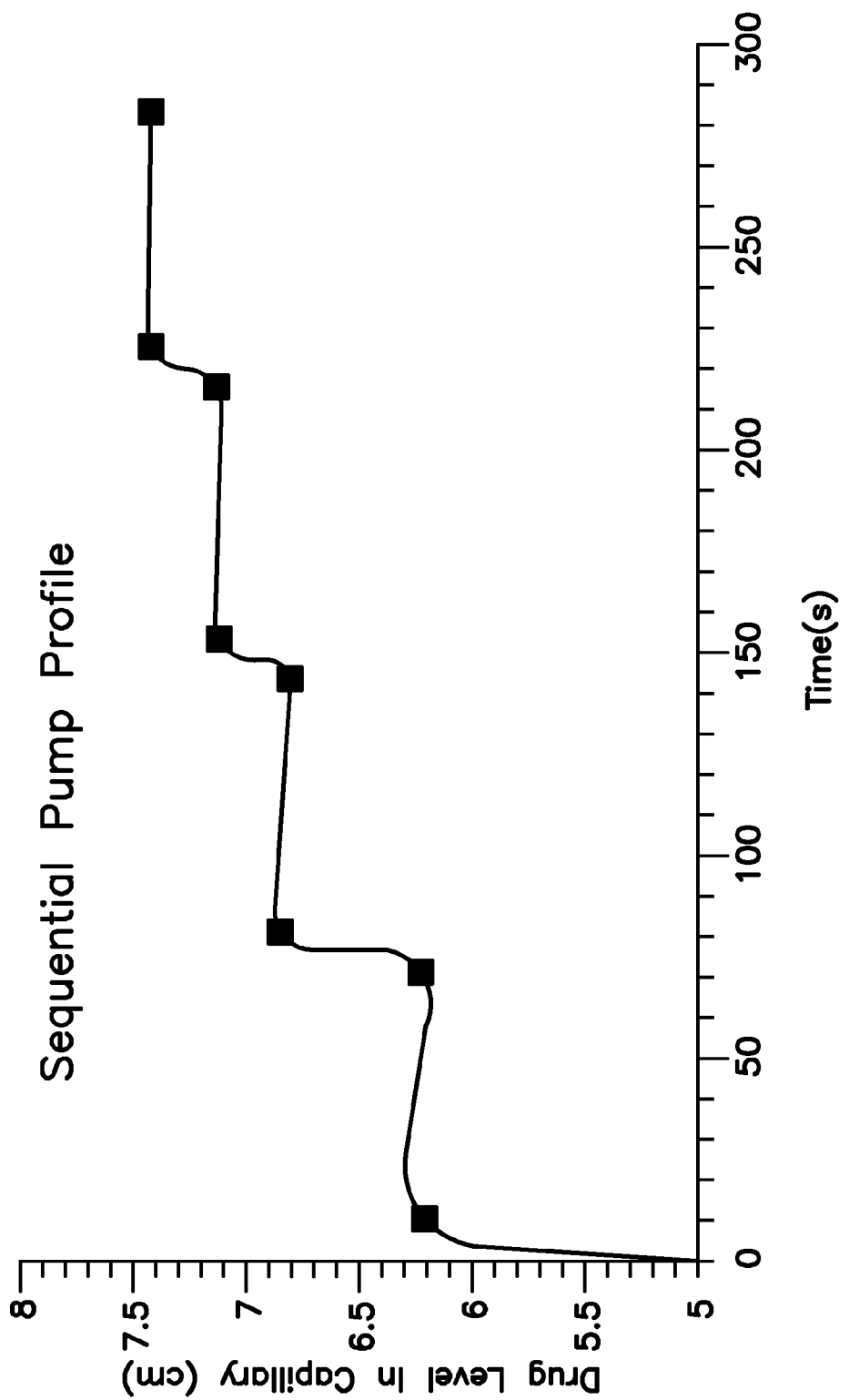
FIG. 15 depicts a graph of height, measured in centimeters (cm), of a liquid in a capillary tube coupled to the transdermal micropump of FIGS. 12 and 13 vs. time, measured in seconds (sec)

Once the subject reapplies heat to the thermally conductive substrate 504, the cycle described above repeats, whereby the volume of material in the chamber 508 increases causing deflection into the chamber 511A, which increases the pressure in the chamber 511B causing deflection into the chamber 514, which causes additional compound to be pumped out. Referring to FIG. 15, a graph of height of a liquid in a capillary tube coupled to the micropump 500 versus time is depicted. As is clearly shown, the liquid in the capillary is sequentially pumped from the micropump 500 in response to the subject sequentially applying heat by touching the thermally conductive substrate 504.

The above embodiments of a transdermal drug compound delivery micropump device according to the present disclosure are directed to dispensing a previously-prepared drug compound. As such, the application of these micropumps is limited to the shelf life of the drug compound. Therefore, it is desirable to provide a micropump that can mix a dry form of a drug compound with water or another activating agent to activate the compound when needed by a subject and subsequently pump the activated drug compound into the vascular system of the subject.

Figure 16:
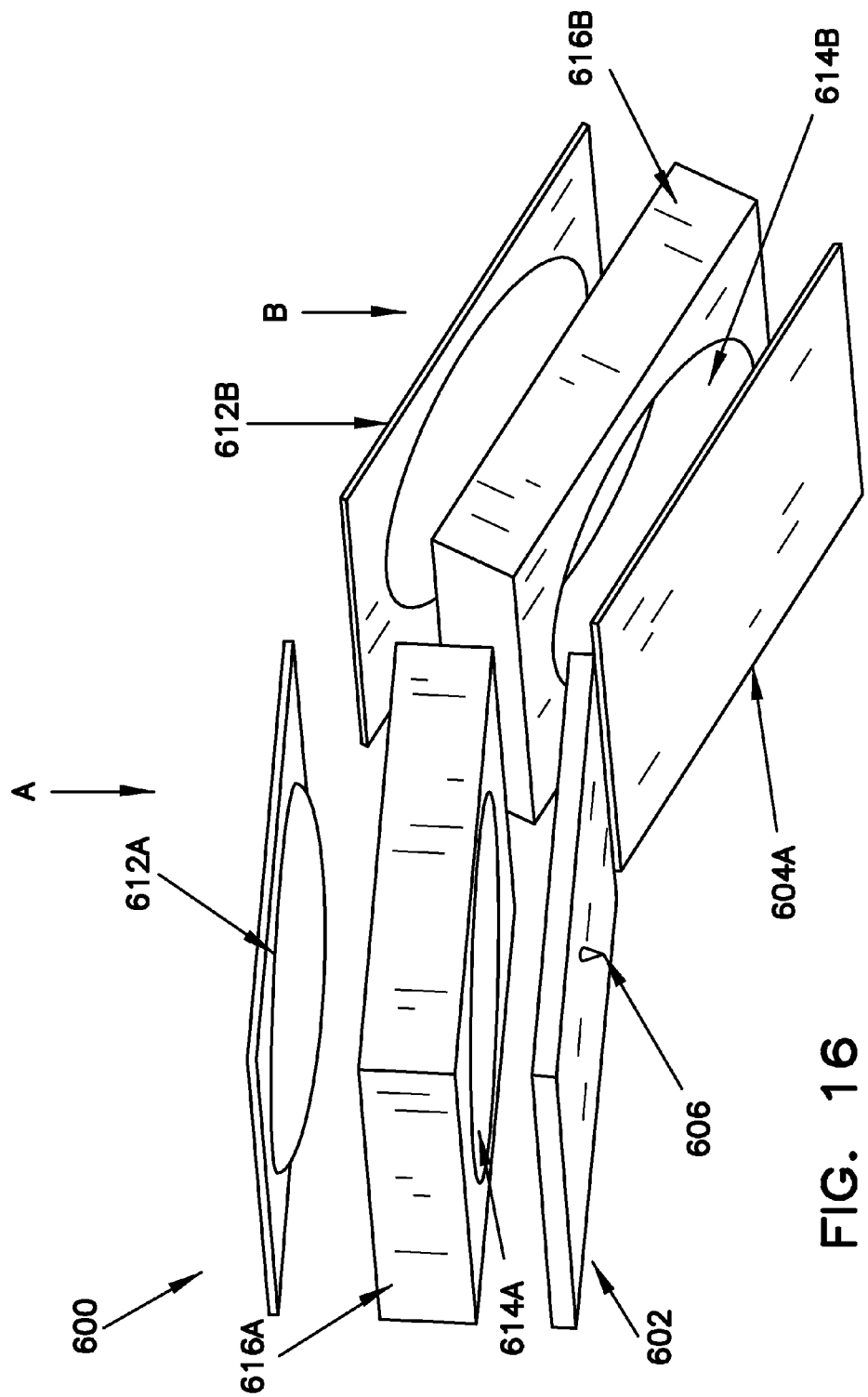

Referring to FIGS. 16 and 17, an embodiment of a mixer-transdermal micropump 600 according to the present disclosure is depicted. The mixer-transdermal micropump 600 includes two halves, A and B, as depicted in FIGS. 16 and 17. The half A of the mixer-transdermal pump 600 includes a needle substrate 602, a chamber 614A, a chamber wall 616A, and a deformable dimple layer 612A. The needle substrate 602 is comprised of at least one needle 606 or an array of needles (not shown). On one side of the needle substrate is the chamber 614A formed by the chamber wall 616A, wherein the interior space of the chamber 614A is in fluid communication with the needle 606. The chamber 614A is capped by the deformable dimple layer 612A, which is in contact with the chamber 614A. The deformable membrane 612A and the needle substrate 602 are configured to maintain a dry (i.e., inactive) form of a drug compound that is disposed in the chamber 614B until the mixer-transdermal micropump 600 is used as described.

The half B of the mixer-transdermal pump 600 includes a membrane substrate 604, a chamber 614B, a chamber wall 616B, and a deformable dimple layer 612B. The deformable dimple layer 612B and the membrane substrate 604 are configured to maintain a fluid that is disposed in the chamber 614B until, as described further below, the fluid in the chamber 614B is allowed to enter the chamber 614A. The chamber 614B is formed by the chamber wall 616B and is capped by the deformable dimple layer 612B on the one side and the membrane substrate 604 on another side.

A film strip 608 connects the two halves, A and B. The film strip 608 is configured to allow the halves A and B to pivot about each other along an axis defined by the film strip 608.

The operation of the mixer-transdermal micropump 600 is described with respect to FIGS. 18A-18F. In operation, the chamber 614B is filled with sterile water or some other activating agent while the dry or inactive drug compound is positioned within the chamber 614A, as depicted in FIG. 18A. Initially, the two halves A and B are adjacent one another, making contact only via the film strip 608. In this position, the deformable dimple layer 612A is inwardly deflected while the deformable dimple layer 612B is outwardly deflected. The subject then rotates the half B under the half A, as depicted in FIG. 18B, such that the needle 606 penetrates the membrane substrate 604, thereby placing the chambers 614A and 614B in fluid communication with each other (as depicted in FIG. 18C). The subject then depresses the deformable dimple layer 612B, which transfers the water or other activating agent from the chamber 614B and into the chamber 614A, wherein the water or other activating agent is mixed with a dry or inactive form of the drug compound. When the subject depresses the deformable dimple layer 612B, deflecting it from the outwardly deflected position to an inwardly deflected position, the deflectable dimple layer 612A deflects outwardly from the inwardly deflected position due to the pressure exerted by the fluid entering the chamber 614A (as depicted in FIG. 18D). The mixing of the drug compound with the activating agent can be accelerated by shaking the mixer-transdermal micropump 600 when the assembly is in the position depicted in FIG. 18D.

Once adequate mixing has occurred, the subject rotates the half B away from contact with half A as depicted in FIG. 18E. Having completed the foregoing steps, the chamber 614A now includes a ready-to-use drug compound (i.e., a combined mixture of previously-inactive drug compound with an activating agent, such as sterilized water) with the associated deformable dimple 612A in the outwardly position. The subject then places the mixer-transdermal pump 600 on the skin and depresses the deformable dimple 612A, as depicted in FIG. 18F, thereby transferring the compound in the chamber 614A into the capillaries of the vascular system and the blood stream of the subject the blood stream via the needle 606. Of course a phase-change embodiment, as discussed above, can be used which requires the subject to simply touch the deformable dimple 612A causing a phase-change to occur, which then causes the mixed drug compound to be delivered to the blood stream without the need to actually press on the deformable dimple 612A.

In the touch-actuated transdermal pump embodiments according to the present disclosure, once the source of heat is removed, the pressure acting on the drug compound disposed within the associated chamber is also removed, thereby causing a cessation of pumping. However, it is desirable to provide a transdermal pump that is configured to provide continued pressure and thereby continued pumping of the compound after the heat source is removed.

Figure 19:
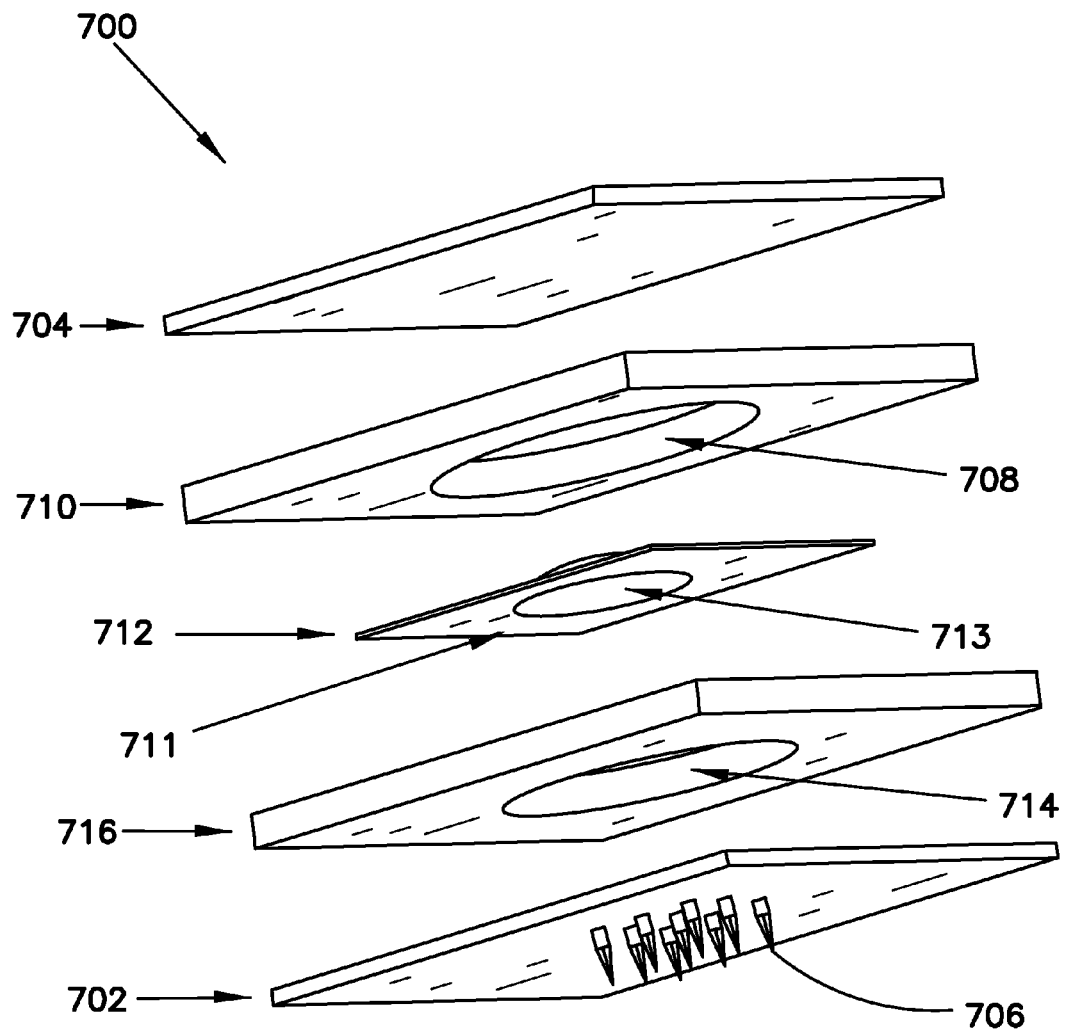
FIGS. 19 and 20 depict an exploded view and a side view of another embodiment of a transdermal micropump according to the present disclosure.
Figure 20:
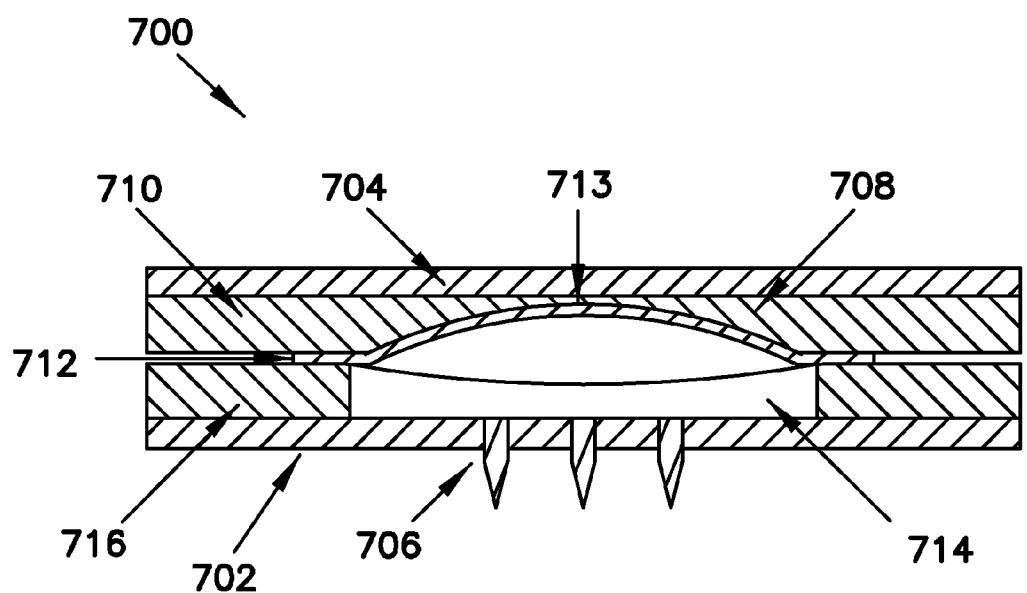

Another embodiment of a transdermal drug compound delivery micropump device 700 according to the present disclosure is capable of providing continued pumping of a compound after the heat source has been removed. Shown in FIGS. 19 and 20 are an exploded view and a side view of one particular embodiment. The micropump 700 includes a needle substrate 702, a first chamber 714, a first wall 716, a dimple assembly 711, a second chamber 708, a second wall 710, and a thermally conductive substrate 704.

The needle substrate 702 includes at least one needle or an array of needles 706. The needle substrate 702 is in contact with the interior space of the chamber 714. The chamber 714 is enclosed by the wall 716. The wall 716 is rigid and can be made from PDMS. The chamber 714 is configured to store a drug compound to be pumped from the micropump 700. On another side, the interior space of the chamber 714 is in contact with the deformable dimple assembly 711. The deformable dimple assembly 711 includes a flat member 712 and a deformable dimple 713, which may be integrally formed with each other. A volume of air can be formed under the deformable dimple 713 and above the compound disposed in the chamber 714. The deformable dimple 713 is made from a material that, once deformed by application of a force, retains its deformed state after the force is removed.

Furthermore, on one side, internal space of the chamber 708 is in contact with the deformable dimple assembly 711. The chamber 708 is enclosed by the wall 710. The wall 710 is rigid and can be made from PDMS. The interior space of the chamber 708 is in contact with a thermally conductive substrate 704. The chamber 708 is configured to store a material that readily and substantially changes volume in response to heat, such as a phase-change material that changes phase (e.g., from a liquid to a gas) due to transferred heat. The material in the chamber 708 is exposed to heat by a subject touching the thermally conductive substrate 704, which transfers heat from the skin of the subject to the material in the chamber 708.

In use, once the subject transfers heat to the material in the chamber 708 by touching it or by applying an external heat source to the thermally conductive substrate 704, the material increases its volume causing the deformable dimple 713 of the dimple assembly 711 to deflect in the chamber 714. Deflection of the deformable dimple 713 applies pressure to the compound in the chamber 714 causing pumping of the compound through the needle array 706. Once the deformable dimple 713 is sufficiently deflected, it permanently retains its deflected form. FIG. 20 depicts the deformable dimple 713 in its deformed state. In this deformed state, air between the deformable dimple 713 and the compound is pressurized, resulting in continued pumping of the compound. Since the deformable dimple 713 is permanently deformed, even if the subject ceases contact with the thermally conductive substrate 704, the deformed dimple continues to apply pressure and thereby pumping of the drug compound.

Figure 21:
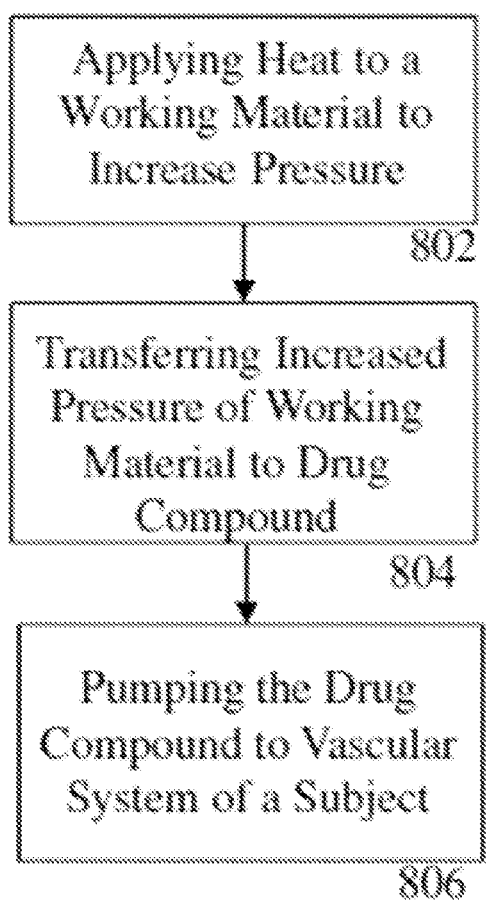
FIG. 21 depicts a block diagram for a method of pumping a drug compound to the vascular system of a subject.

Referring to FIG. 21, a block diagram for a method 800 for pumping a drug compound by a transdermal pump is depicted. The method 800 includes applying heat to a working material positioned in a first chamber (identified by block 802). The working material is configured to increase volume and thereby pressure in response to the application of heat. The method 800 further includes transferring the increase in pressure from the working material to a drug compound positioned in a drug compound chamber (identified by block 804). The method 800 further includes pumping the drug compound through at least one needle to a vascular system of a subject in response to the transferred pressure (identified by block 806).

Those skilled in the art will recognize that numerous modifications can be made to the specific embodiments described above. Therefore, the following claims are not to be limited to the specific embodiments illustrated and described above. The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

The invention claimed is:

1. A micropump device, comprising:
   a first layer forming a first chamber storing a working material;
   a second chamber defined by a deflectable membrane separating the second chamber from the first chamber and configured to deflect in response to a volume increase in the first chamber, the second chamber storing a drug compound to be delivered to a subject's vascular system; and
   at least one needle in fluid communication with the second chamber and configured to penetrate a subject's skin to pump the drug compound in response to deflection of the deflectable membrane;
   wherein the working material in the first chamber is a phase-change material that increases in volume in response to application of heat from a user's skin to the first layer,
   the deflectable membrane in fluid contact with the phase-change material in the first chamber and in fluid contact with the drug compound in the second chamber.

2. The micropump of claim 1, wherein the working material in the first chamber contains a mixture of yeast and a water-based sugar solution.

3. The micropump of claim 1, wherein the first layer and a material defining the second chamber are made of composite material.

4. The micropump of claim 3, wherein the composite material is polydimethylsiloxane.

5. The micropump of claim 1, further comprising:
   a third chamber formed by a cap layer and in fluid communication with the second chamber, the third chamber configured to support and provide fluid communication to a plurality of needles; and
   at least one channel formed between the second chamber and the third chamber for delivery of the drug compound from the second chamber to the third chamber.

6. The micropump of claim 1, wherein the first layer is i) formed of a thermally conductive substrate, or ii) in contact with a thermally conductive substrate.

7. The micropump of claim 6, wherein material of each of the thermally conductive substrates is one of a metal and silicon.

8. The micropump of claim 1, wherein the volume increase in the first chamber is at a rate of between 33.7 µL/min and 60.1 µL/min.

* * * * *